US011771824B2

(12) United States Patent
Pizzochero et al.

(10) Patent No.: US 11,771,824 B2
(45) Date of Patent: Oct. 3, 2023

(54) FORCE SENSING RESISTOR FOR LIQUID LOW-VOLUME DETECTION AND OCCLUSION SENSING AND METHODS AND APPARATUSES FOR FLOW SENSING ALONG FLUID PATH IN FLUID DELIVERY DEVICE

(71) Applicant: Becton, Dickinson and Company, Franklin Lakes, NJ (US)

(72) Inventors: Alessandro Pizzochero, Chelmsford, MA (US); J. Richard Gyory, Sudbury, MA (US); Joseph Iskandar, Brighton, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 5 days.

(21) Appl. No.: 17/408,180

(22) Filed: Aug. 20, 2021

(65) Prior Publication Data

US 2021/0379281 A1   Dec. 9, 2021

Related U.S. Application Data

(63) Continuation of application No. 15/529,135, filed as application No. PCT/US2015/064028 on Dec. 4, 2015.

(Continued)

(51) Int. Cl.
*G01L 9/00*         (2006.01)
*A61M 5/168*        (2006.01)
(Continued)

(52) U.S. Cl.
CPC .... *A61M 5/16854* (2013.01); *A61M 5/14248* (2013.01); *A61M 5/16831* (2013.01);
(Continued)

(58) Field of Classification Search
CPC ..................................... G01L 9/0001
See application file for complete search history.

(56) References Cited

U.S. PATENT DOCUMENTS

| 4,236,880 A | 12/1980 | Archibald |
| 5,807,322 A | 9/1998 | Lindsey et al. |

(Continued)

FOREIGN PATENT DOCUMENTS

| JP | 2001517964 A | 10/2001 |
| JP | 2002126092 A | 5/2002 |

(Continued)

OTHER PUBLICATIONS

International Search Report and Written Opinion dated Feb. 11, 2016 which issued in Application No. PCT/US2015/064028.

(Continued)

*Primary Examiner* — Alexander A Mercado
(74) *Attorney, Agent, or Firm* — Dickinson Wright PLLC

(57) ABSTRACT

A system and method is provided for detecting fluid low-volume and occlusion in a device using force sensing resistor (FSR) sensor. One or more force sensing resistors are positioned in communication with a fluid channel at one or more of a pump intake and pump outlet to detect pressure in the fluid channel. The pressure is detected through communication with the force sensing resistor and indicates an irregular system condition including but not limited to, fluid low-volume level and occlusion. Also provided are a fluid flow sensor (e.g., FSR or MEMS sensor) disposed relative to an embedded fluid channel in the base of a wearable medicine delivery pump.

10 Claims, 26 Drawing Sheets

Related U.S. Application Data

(60) Provisional application No. 62/087,775, filed on Dec. 4, 2014.

(51) Int. Cl.
    *A61M 5/142*     (2006.01)
    *G01L 9/02*     (2006.01)
    *G01F 1/696*     (2006.01)
    *G01L 1/20*     (2006.01)

(52) U.S. Cl.
    CPC ............ *G01F 1/696* (2013.01); *G01L 1/20* (2013.01); *G01L 9/02* (2013.01); *A61M 2005/16863* (2013.01); *A61M 2205/332* (2013.01); *A61M 2205/3331* (2013.01); *A61M 2205/3368* (2013.01); *A61M 2205/3386* (2013.01); *A61M 2205/50* (2013.01); *A61M 2205/502* (2013.01)

(56) References Cited

U.S. PATENT DOCUMENTS

| | | |
|---|---|---|
| 2008/0051698 A1 | 2/2008 | Mounce et al. |
| 2009/0062768 A1* | 3/2009 | Saul .................. A61M 5/16877 604/506 |
| 2009/0158853 A1* | 6/2009 | Berner .................. G01L 19/147 356/480 |
| 2011/0160652 A1 | 6/2011 | Yodfat et al. |
| 2012/0197197 A1 | 8/2012 | Iddan et al. |
| 2014/0163339 A1 | 6/2014 | Goldstein et al. |
| 2014/0194812 A1 | 7/2014 | Amirouche et al. |
| 2014/0212986 A1 | 7/2014 | Angelescu et al. |
| 2014/0236117 A1 | 8/2014 | Dutcher |
| 2014/0309589 A1* | 10/2014 | Momose ........... A61M 5/14248 604/151 |
| 2015/0192478 A1* | 7/2015 | Rueth ...................... G01L 9/00 374/143 |
| 2017/0340814 A1* | 11/2017 | Miesel .................. G01L 15/00 |

FOREIGN PATENT DOCUMENTS

| | | |
|---|---|---|
| JP | 2007520270 A | 7/2007 |
| JP | 2014200617 A | 10/2014 |

OTHER PUBLICATIONS

Japanese Office Action dated Sep. 24, 2019, which issued in the corresponding Japanese Patent Application No. 2017-529760, including English translation.

* cited by examiner

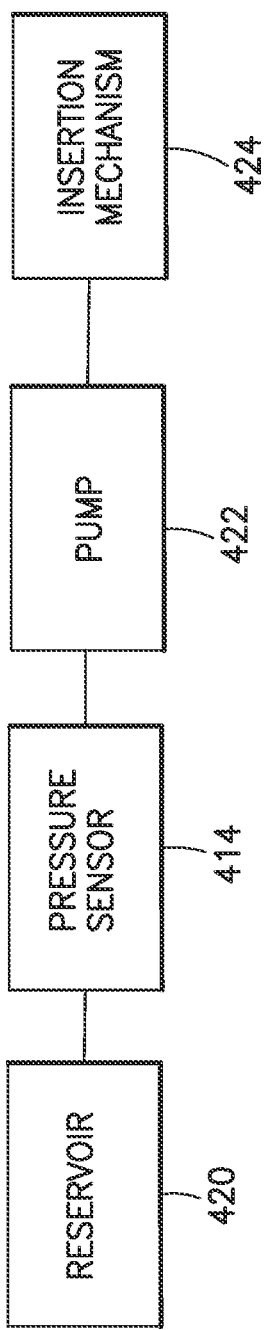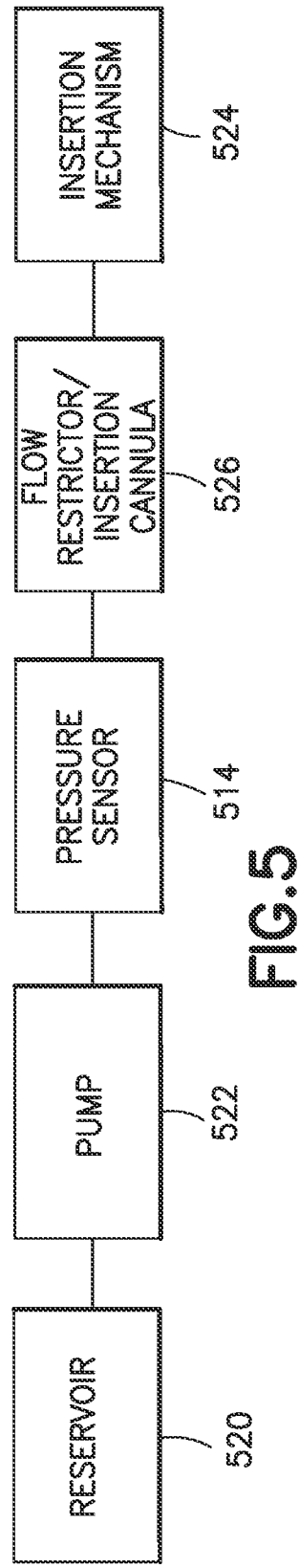

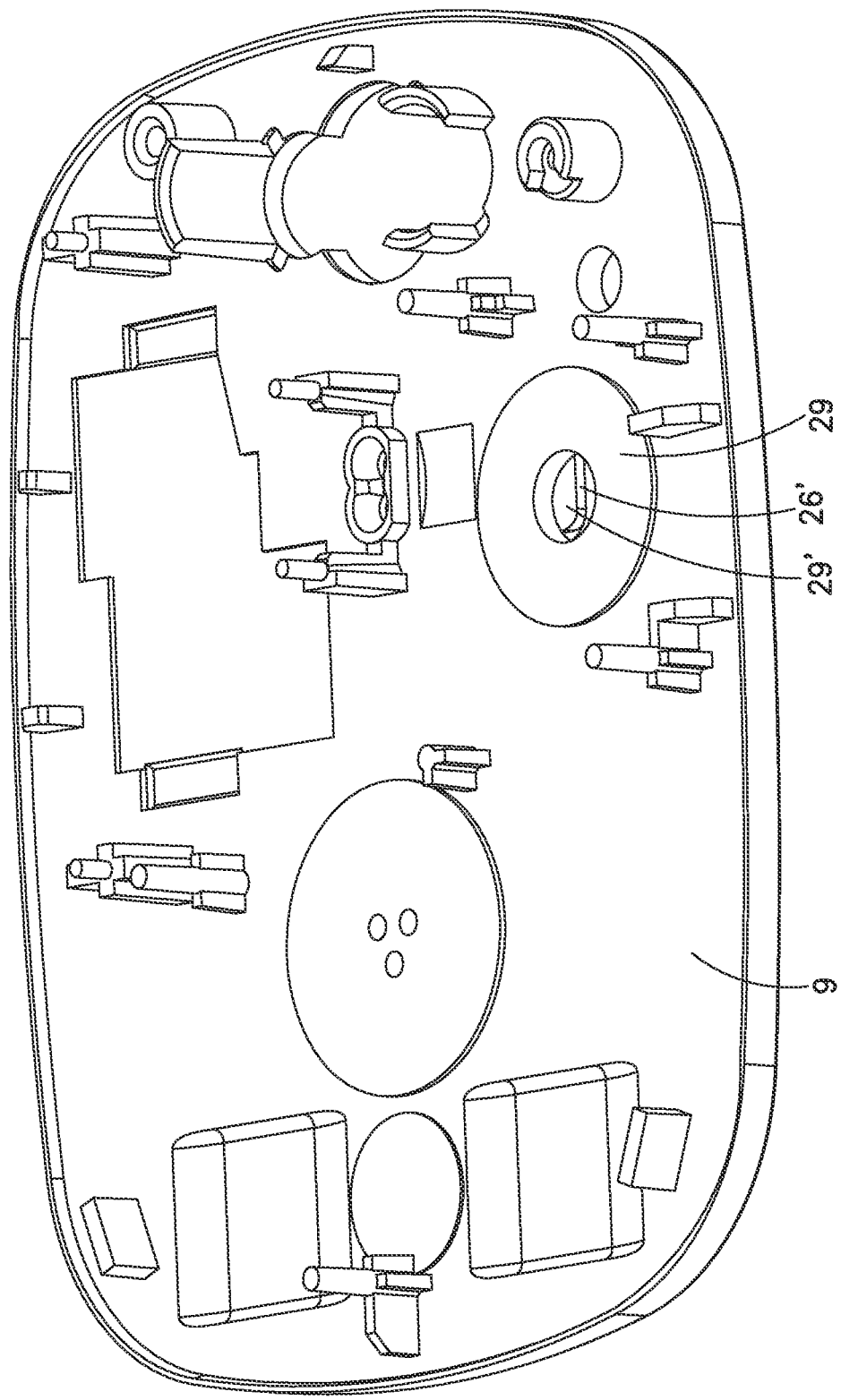

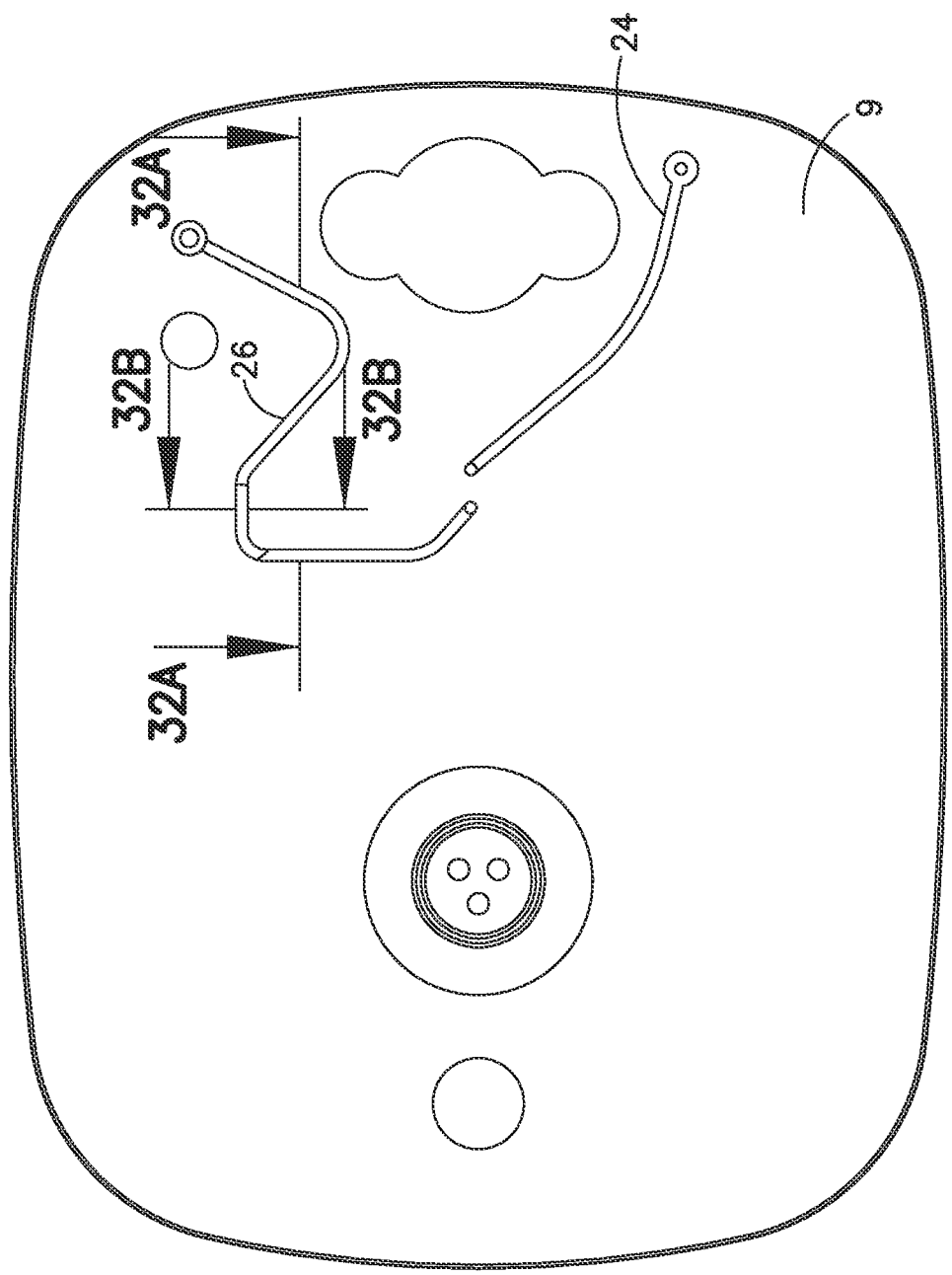

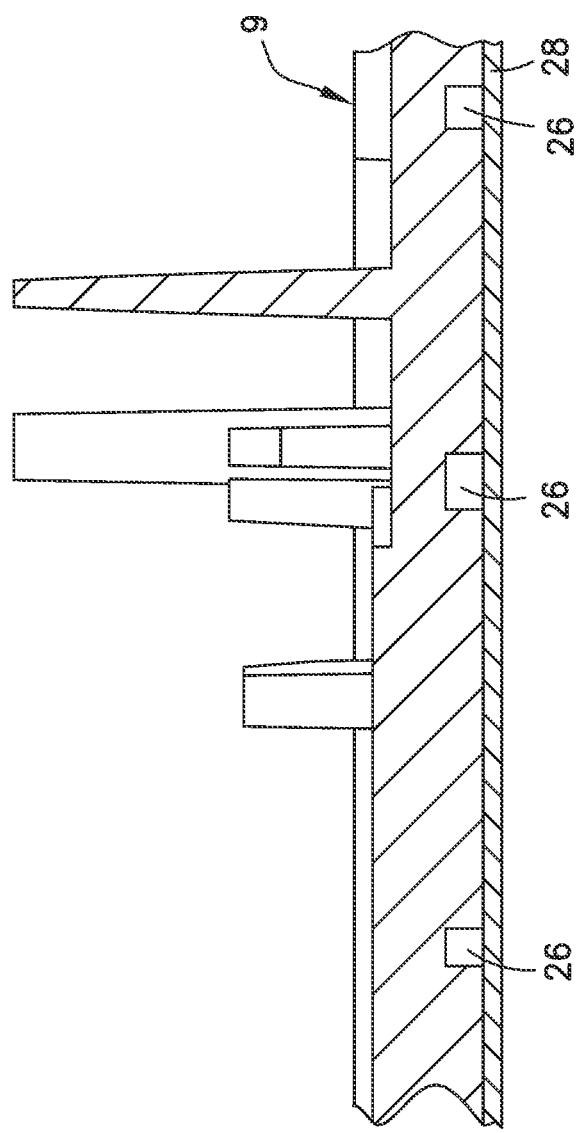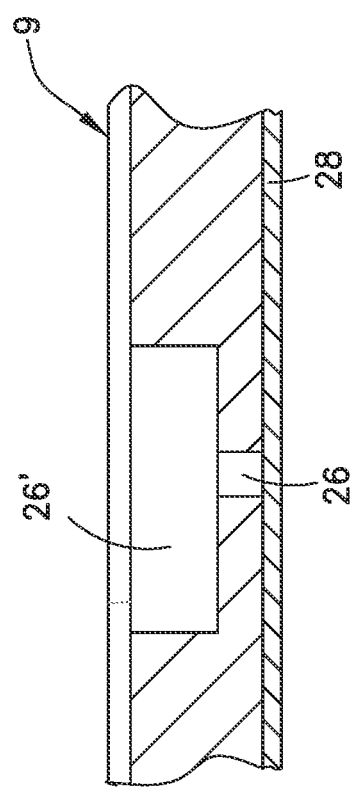

FORCE SENSING RESISTOR FOR LIQUID LOW-VOLUME DETECTION AND OCCLUSION SENSING AND METHODS AND APPARATUSES FOR FLOW SENSING ALONG FLUID PATH IN FLUID DELIVERY DEVICE

This application is a continuation application of U.S. patent application Ser. No. 15/529,135, filed May 24, 2017, which is a 35 U.S.C. 371 application of PCT Application No. PCT/US2015/064028, filed Dec. 4, 2015, which claims the benefit of U.S. Provisional Application Ser. No. 62/087,775, filed Dec. 4, 2014, the entire contents of which are hereby incorporated herein by reference.

FIELD OF THE INVENTION

The present invention relates to systems and methods for detecting fluid low-volume and occlusion in a device using force sensing resistors and flow sensing in medication delivery systems. For example, one or more force sensing resistors are positioned in communication with a fluid channel at one or more of a pump intake and pump outlet to detect pressure in the fluid channel. The pressure is detected through communication with the force sensing resistors and indicates an irregular system condition including, but not limited to, fluid low-volume and occlusion. Other flow sensing devices can be employed relative to a fluid path in a pump or other fluid delivery device.

BACKGROUND OF THE INVENTION

Occlusion of a fluid path is a complication where either the delivery to or withdrawal of fluid from a patient is partially or completely restricted. These include devices for subcutaneous (SC), intramuscular (IM), intradermal (ID) and intravenous (IV) delivery, access and sampling. For example, in an ambulatory insulin infusion system, both basal rate and bolus delivery of a medication fluid to a patient is typically provided by delivery of micro-boluses or fluid pulses through a fluid path (e.g., a tube) to generate the composite target total delivery volume and rate, and delivered to the patient via an infusion set. Generally, the boluses during the basal infusion are periodically delivered in short pulses over a regular interval (such as a period of 3 minutes) via a servo motor that actuates a piston. The actuated piston moves and biases the fluid in a fluid reservoir, thereby decreasing volume in the fluid reservoir and causing a controlled amount of medication fluid to flow from the fluid reservoir and into the fluid path. The infusion set receives the fluid flow and communicates the fluid into the patient. After delivering the bolus, the system waits for the period to expire to initiate a next delivery of medication. During delivery of higher volumes (such as for post-prandial meal boluses), the size of the small individual pulses may be increased and/or the time interval decreased to provide a greater total fluid volume and increased delivery rate.

As the fluid flows through the tube toward the infusion set, the induced pressure in the infusion system decays as a result of losses due to mechanical forces (e.g., static and dynamic friction, and so on). Further, other external or internal factors may further impede the flow of fluid. A partial kink in the tubing would reduce cross-sectional area in the fluid path, thereby reducing the rate of fluid able to traverse the fluid path and increasing pressure in the fluid path. The fluid path may be impeded by other factors such as crystal formation in the fluid, the presence of gaseous bubbles, impurities or other particles, backpressure from tissues in the patient, physical movement of the patient, movement of the fluid path, non-compliance of elastomeric components in the fluid path, and so on. When the fluid path is disrupted by any internal or external reason, the fluid path may experience a complete or partial occlusion that affects delivery of the medication fluid to the patient. In a similar adverse manner, a fluid reservoir low-volume level also affects delivery of the medication fluid to the patient.

The flow of the medication fluid in the fluid path is currently detected by measuring the force applied to the piston during piston actuation as described above. However, the force applied to the piston can reflect static and dynamic friction forces associated with the piston mechanism in addition to pressure in the fluid path. Thus, the force applied to the piston represents the combined static friction, dynamic friction, and other mechanical forces in addition to fluid pressure. The fluid pressure may in fact be a relatively small component of the overall force applied to reservoir piston, and accordingly piston force is not necessarily directly correlated to the pressure in the fluid path at the location of medication delivery. As a result, sensitivity is limited in these types of systems since the static and dynamic friction forces within the fluid reservoir dominate below approximately 2 psi. It may take multiple piston movements to determine that there is a fluid low-volume level or an occlusion occurring in the fluid path that is presently affecting medication delivery. Further, in the event that the pressure of the fluid reservoir is low, the static and dynamic friction forces associated with piston movement may be larger than the force required to move the liquid, thereby causing the pressure measurements during piston movement to be inaccurate and prevent detection of fluid low-volume levels or occlusions.

Occlusion events are responsible for premature removal of 5-15% of vascular access devices such as peripheral intra venous catheters (PIVCs) that are used both for patient fluid sampling and medication delivery. Evidence suggests that timed or scheduled removal of PIVC catheters without cause may not benefit patients and may add cost to healthcare treatment. In a PIVC catheter, occlusion may be a result of mechanical phenomena such as kinking or impingement of the catheter tip against the intima, biochemical effects such as precipitation of the infusate, and thrombus formation. In particular, thrombus aggregation in a catheter may cause an occlusion event that leads to other complications such as phlebitis. In a PIVC catheter, blood can enter the catheter during events such as placement of the catheter, as a result of pressure changes from movements of the catheter or associated tubing, during checks performed by medical staff, as a result of improper or incomplete flushing of the catheter, or via blood sampling. Each blood exposure event in the catheter can lead to build up of thrombus within or around a catheter to form a clot that reduces the diameter of the flow path. Consequently, more pressure is needed to deliver the same amount of fluid at a given rate with potentially dangerous consequences for the patient.

In conventional systems, a fluid low-volume level or an occlusion in the fluid path may be detected too slowly or not at all in some circumstances, with potentially dangerous consequences for the patient. For instance, if an undetected fluid low-volume level or occlusion occurs during insulin infusion, the patient may not receive a necessary amount of medication to prevent a potentially dangerous hyperglycemic event. Because the delivery of the medication fluid may be vital in delivery of medical service, there is a need for rapid detection of fluid low-volume levels and occlusions in medication delivery systems.

Accordingly, improved flow sensing is needed for accurate detection of fluid low-volume levels or occlusions. In addition, other flow sensing means are needed for different fluid delivery devices such as a patch pump or other device that does not employ a piston and cannot rely on measuring the force applied to a piston during piston actuation for flow sensing. Further, flow sensors that are in contact with the fluid can require rigorous testing and regulatory approval to ensure the sensors are biocompatible with the fluid. A need therefore also exists for medication delivery devices wherein a flow sensor need not come into direct contact with the fluid in the fluid path.

SUMMARY OF THE INVENTION

It is therefore an object of embodiments of the present invention to provide a system and method to satisfy the above needs, and provide for the rapid detection of fluid low-volume levels and occlusions in medication delivery systems.

It is another object of embodiments of the present invention to provide a system and method for detecting occlusions in a medication fluid communication system or venous access device comprising a fluid reservoir, a fluid path connected between the fluid reservoir and a patient, a fluid delivery mechanism, and a pressure sensor measuring a pressure of the fluid within the fluid path. The method includes measuring pressure of a medication fluid in a fluid path of a medication delivery system using a force sensing resistor. Based on the pressure measurements, the system and method determines if a flow of the medication fluid is successful, reduced, or unsuccessful.

Also disclosed is another system and method for detecting fluid low-volume levels in a medication fluid communication system or venous access device comprising a fluid reservoir, a fluid path connected between the fluid reservoir and a patient, a fluid delivery mechanism, and a pressure sensor measuring a pressure of the fluid within the fluid path. The method includes measuring pressure of a medication fluid in a fluid path of a medication delivery system using a force sensing resistor. Based on the pressure measurements, the system and method determines if a level of the medication fluid is low.

These and other objects are substantially achieved by providing, in accordance with embodiments of the present invention, a system and method for detecting fluid low-volume and occlusion in a device using force sensing resistors. The system and method is applicable to a device comprising a fluid reservoir, a fluid path connected between the fluid reservoir and a patient, a fluid delivery mechanism, and a pressure sensor measuring a pressure of the fluid within the fluid path. One or more force sensing resistors are positioned in communication with a fluid channel at one or more of a pump intake and pump outlet to detect pressure in the fluid channel. The pressure is detected through communication with the force sensing resistors and indicates an irregular system condition including but not limited to, fluid low-volume and occlusion.

In accordance with aspects of illustrative embodiments of the present invention, a fluid delivery system comprises a fluid reservoir; a pump that controls the flow of fluid from the fluid reservoir to a patient via a fluid path; a sensor located along the fluid path to detect fluid flow or pressure; and a processor configured to control the pump to deliver the fluid to the patient and to receive sensor data from the sensor. The sensor comprises a protrusion on an enclosure. The protrusion is configured to extend into a cavity provided in the fluid path to allow contact between the fluid and the sensor to detect the fluid flow or pressure. The enclosure has electronics for generating sensor data corresponding to the detected fluid flow or pressure, the enclosure configured to be connected to the processor to provide the sensor data to the processor.

In accordance with aspects of illustrative embodiments, the sensor is provided with a gel to protect the electronics from the fluid.

In accordance with aspects of illustrative embodiments, the sensor is a pressure sensor. For example, the sensor is a force sensing resistor-type sensor, and the fluid in the cavity contacts the exterior of the sensor and pressure is determined from changes in pressure on a surface of the force sensing resistor sensor.

In accordance with aspects of illustrative embodiments, the sensor is positioned in communication with the fluid at one or more of a pump intake and a pump outlet associated with the pump.

In accordance with aspects of illustrative embodiments, the fluid delivery system further comprises an insertion mechanism for inserting a cannula into the skin of the patient to deliver the fluid. The sensor is positioned downstream of the pump between the pump and the insertion mechanism to determine pressure at the outlet of the pump.

In accordance with aspects of illustrative embodiments, the fluid delivery system further comprises a planar base that supports the pump and the insertion mechanism. The fluid path comprises at least one channel embedded on a surface of the planar base and extending between the pump and the insertion mechanism.

In accordance with aspects of illustrative embodiments, the fluid delivery system further comprises a fluid channel cover that covers the at least one channel embedded on the surface of the planar base. For example, the fluid channel cover is chosen from a clear film, a foil, a flexible sheet of material, a semi-rigid material, and a rigid material.

Illustrative embodiments and respective aspects thereof can be used with other illustrative embodiments.

Additional and/or other aspects and advantages of the present invention will be set forth in the description that follows, or will be apparent from the description, or may be learned by practice of the invention. The present invention may comprise an I/O and control system and data communication bus protocol and methods for forming and operating same having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The above and other objects and advantages will become apparent upon consideration of the following drawings and detailed description. The illustrative embodiments of the present invention are illustrated in the appended drawings in which like reference numerals refer to like elements and in which:

FIG. 4 is a block diagram illustrating the force sensing resistor placed between the reservoir and pump of the device, in accordance with embodiments of the present invention;

FIG. 5 is a block diagram illustrating the force sensing resistor placed between the pump and delivery end of the device, in accordance with embodiments of the present invention;

FIG. 28 is a perspective top view of a base of a pump that can be employed by the pump of FIG. 27;

FIG. 29 is a bottom view of the base of FIG. 28;

FIGS. 32A and 32B are partial cross-sectional views of the base of a pump in accordance with an embodiment of the present invention.

In the drawing figures, it will be understood that like numerals refer to like structures.

DETAILED DESCRIPTION OF THE ILLUSTRATIVE EMBODIMENTS

Figure 1:
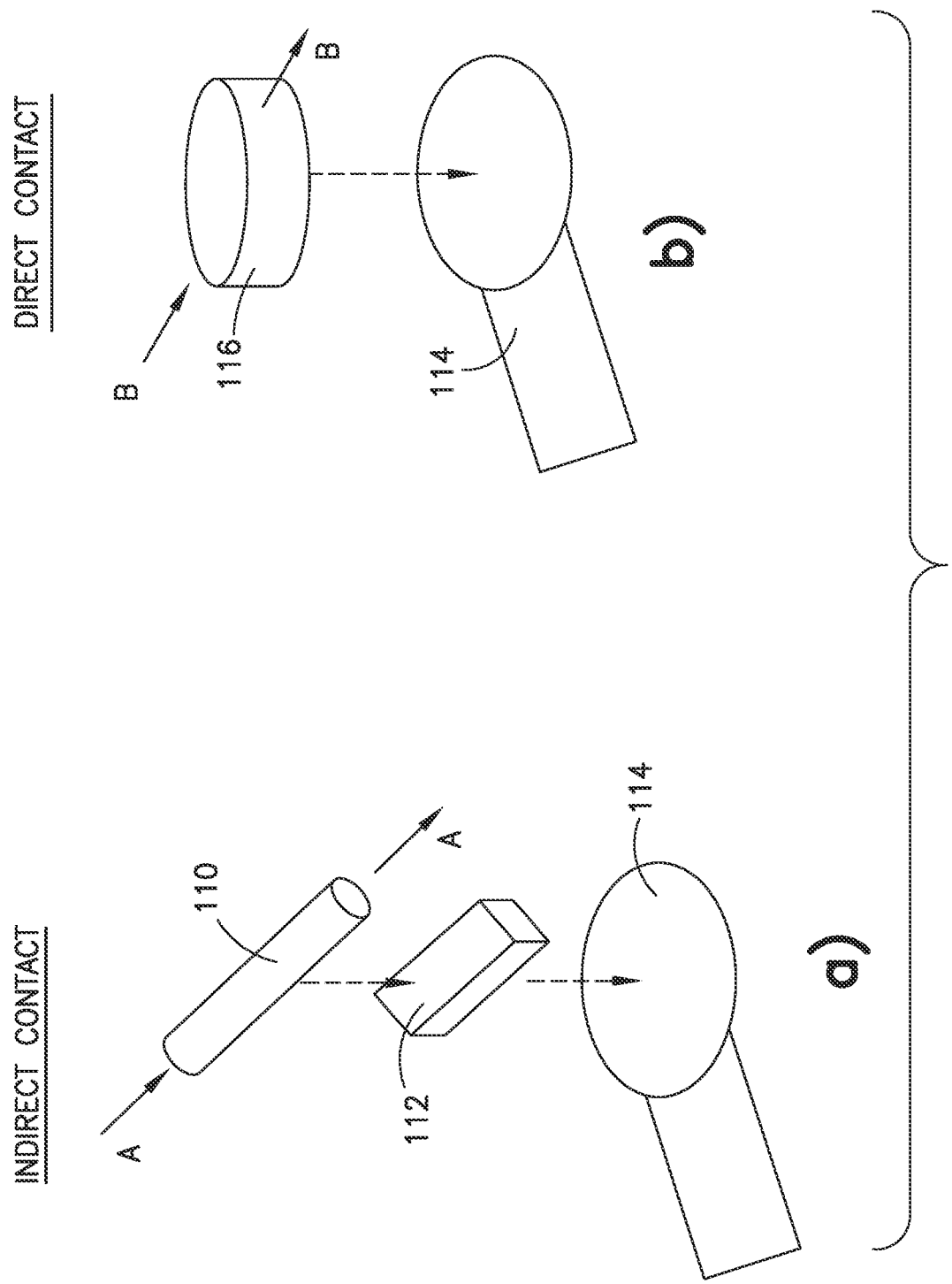
FIG. 1 are views (a) and (b) illustrating an indirect mode of force sensing resistor operation, and illustrating a direct mode of force sensing resistor operation, in accordance with embodiments of the present invention.

The various features of the illustrative embodiments will now be described with reference to the drawing figures, in which like parts are identified with the same reference characters. The following description of the presently contemplated best mode of practicing the invention is not to be taken in a limiting sense, but is provided merely for the purpose of describing the general principles of the invention.

In accordance with illustrative embodiments of the present invention, systems and methods are provided for detecting fluid low-volume and occlusion in a device using force sensing resistor based sensors. To do so, one or more force sensing resistors are positioned in communication with a fluid channel at one or more of a pump intake and pump outlet to detect pressure in the fluid channel as illustrated in FIGS. 4 and 5, respectively. The pressure is detected through indirect or direct fluid communication with the force sensing resistors (e.g., a force corresponding to pressure exerted over a selected surface area) and processes to determine if an irregular system condition has occurred including, but not limited to, fluid low-volume and occlusion.

First Illustrative Embodiment: Low-Volume Indicator

A first embodiment is directed toward a system and method for detecting fluid low-volume in a device using force sensing resistors. A force sensing resistor is a sensing device that is characterized by a varying conductance in response to force applied to its surface. The response is generally linear over a large operating range, thereby making such force sensing resistors ideal for the following embodiments in which one or more force sensing resistors are positioned in communication with a fluid channel at one or more of a pump intake and pump outlet to detect pressure, including reductions in pressures and buildups of pressures in the fluid channel. The pressure is detected through communication with the force sensing resistors and can be interpreted to quickly and accurately identify irregular system conditions.

As noted in greater detail below, the system and method is applicable to a device comprising a fluid reservoir, a fluid path connected between the fluid reservoir and a patient, a fluid delivery mechanism, and a pressure sensor measuring a pressure of the fluid within the fluid path. Methods for coupling the fluid to the force sensing resistors have been developed and include direct and indirect configurations as shown in FIG. 1. FIG. 1 includes view (a) illustrating an indirect mode of force sensing resistor operation, and view (b) illustrating a direct mode of force sensing resistor operation in accordance with embodiments of the present invention. An example of an indirect mode of force sensing resistor operation is achieved by running fluid through a compliant tube that is constrained to be in intimate contact with the face of the force sensing resistor. As shown in greater detail in FIG. 2, an intermediate mechanical coupling device can be used to control the interface.

In FIG. 1 view (a) illustrating an indirect mode of force sensing resistor operation, the system includes a flow tube 110 through which a fluid flows in the direction of arrow A. A contact element, or "puck" 112 is disposed between the flow tube 110 and a force sensing resistor 114. That is, the flow tube 110 is positioned against the puck 112, and the puck 112 is positioned against the force sensing resistor 114. Any deformation of the flow tube 110 is communicated indirectly to the force sensing resistor 114 via the puck 112.

The force sensing resistor can be comprised of any suitable device, such as the FSR Model 402 round force sensor from Interlink Electronics™. Force sensing resistors, or FSRs, are robust polymer thick film (PTF) devices that exhibit a decrease in resistance with increase in force applied to the surface of the sensor. This force sensitivity is optimized for use in human touch control of electronic devices such as automotive electronics, medical systems, and in industrial and robotics applications. Custom force sensing resistors can be manufactured in sizes ranging from 5 mm to over 600 mm in diameter in the case of round force sensing resistors, but can also be square or otherwise shaped.

In FIG. 1 view (b) illustrating a direct mode of force sensing resistor operation, the system includes a flow chamber 116 through which a fluid flows in the direction of arrow B. In this embodiment, the flow chamber 116 is positioned against the force sensing resistor 114. Any deformation of the flow chamber 116 is communicated directly to the force sensing resistor 114.

Figure 2:
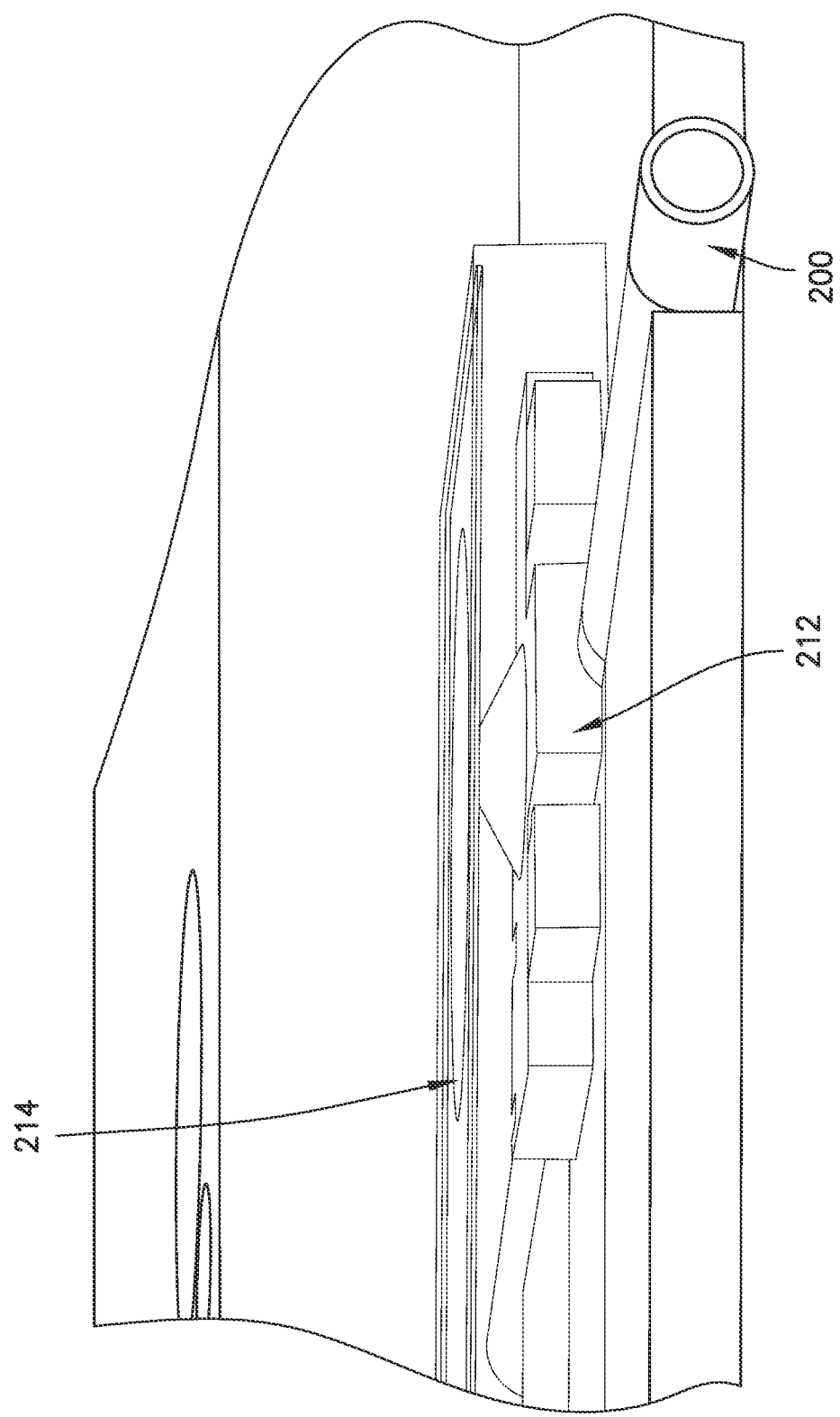
FIG. 2 is a transparent perspective view of an indirect mode of force sensing resistor operation, in accordance with embodiments of the present invention.

FIG. 2 is a transparent perspective view of indirect mode of force sensing resistor operation in accordance with embodiments of the present invention. FIG. 2 illustrates the use of a force sensing resistor 214 in "indirect" contact where fluid flows through a compliant tube 200 and a mechanical energy transfer part, referred to as a "puck" 212, is used to convey pressure to the surface of the force sensing resistor 214. As noted in regard to view (a) of FIG. 1, the tube 200 is positioned against the puck 212, and the puck 212 is positioned against the force sensing resistor 214. Any deformation of the tube 200 is communicated indirectly to the force sensing resistor 214 via the puck 212. The tube, puck and other structural elements of this embodiment, or other embodiments described below, can be constructed of any suitable material such as plastic, but not limited thereto. The puck 212 materials, dimensions and position relative to the fluid channel and the force sensing resistor 214 can vary depending on the desired tolerances for the sensor.

In the embodiment of FIG. 2, the system and method are configured to control pre-loading of the force sensing resistor 214, and ensure that operation limits of the force sensing resistor 214 combined with the associated electronics are not exceeded, resulting in mechanical/electrical saturation or lack of sensitivity. That is, the system and method are configured to operate within the middle, linear operating range of the force sensing resistors 114, 214.

Figure 3:
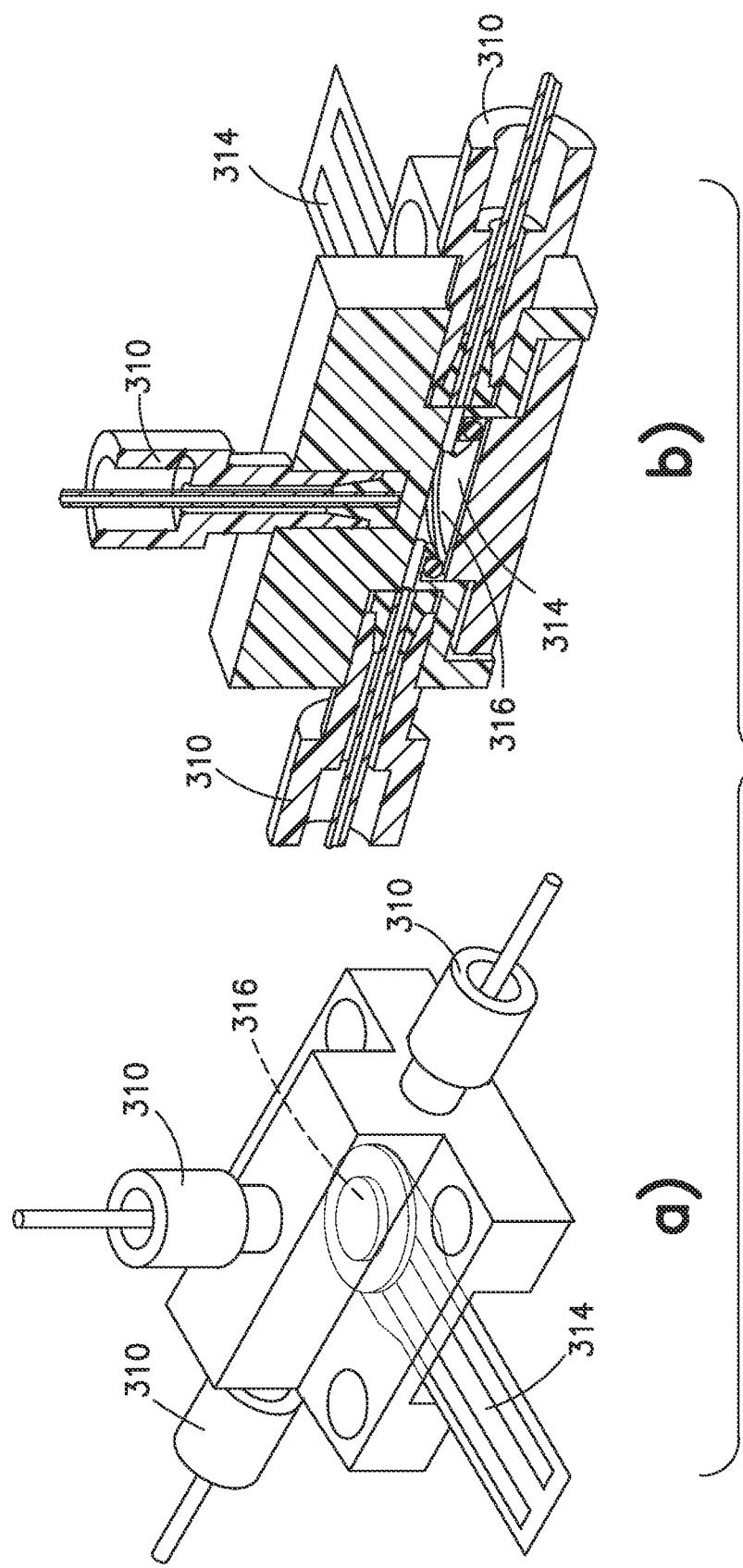
FIG. 3 are views (a) and (b) illustrating a direct mode of force sensing resistor operation, in accordance with embodiments of the present invention.

FIG. 2 illustrates an indirect mode of force sensing resistor operation in accordance with illustrative embodiments of the present invention. On the other hand, an example of direct mode of force sensing resistor operation in accordance with illustrative embodiments of the present invention can be provided by running the fluid into a chamber formed, for example, by the force sensing resistor placed and sealed over a channel/well of predetermined size and shape as shown in FIG. 3. FIG. 3 can be an illustrative testing chamber with two or more flow lines 310. It is to be understood, however, that the sensor 314 and fluid chamber 316 and fluid path 310 configurations can vary in accordance with different embodiments of the present invention such as described below in connection with FIGS. 15-33. For example, the sensor 314 can be disposed adjacent a fluid path in a fluid delivery pump.

FIG. 3 includes view (a) illustrating a transparent perspective view of direct mode of force sensing resistor operation, and view (b) illustrating a cross-sectional view of direct mode of force sensing resistor operation, in accordance with embodiments of the present invention. The views of FIG. 3 show the use of force sensing resistor 314 in "direct" contact where fluid flows in a chamber 316 that is in direct contact with the force sensing resistor 314 surface. Fluid is routed through the chamber through two or more of the flow lines 310. In the direct mode, energy transfer occurs without the need for any intermediate mechanical device, thereby improving signal and assembly tolerances.

In the exemplary embodiments of the present invention, the aspects of the invention include, in part, the use of the force sensing resistor 114, 214, 314 and the means for coupling, directly and indirectly, fluid energy to the force sensing resistor. The characteristics of the coupling are configured so that the mechanical energy from pumping fluid is transferred as deflection, positive or negative, to the force sensing resistor to a degree that is detectable by the combination of force sensing resistor size/shape and associated electronics.

Figure 13:
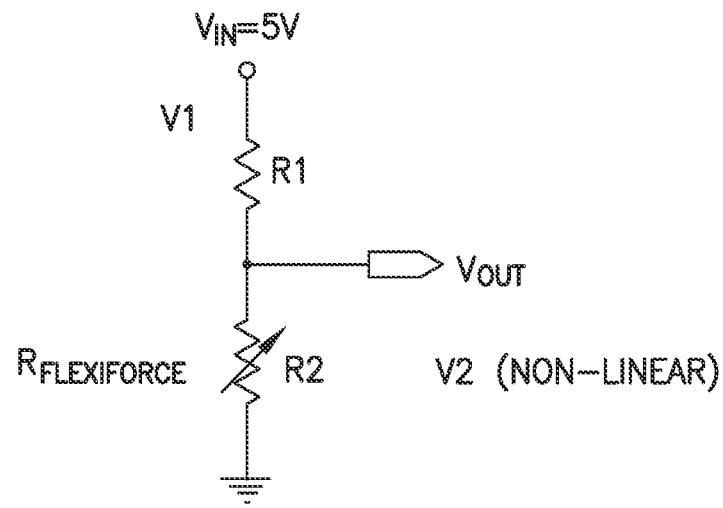
FIG. 13 is an exemplary voltage divider schematic incorporating a force sensing resistor, in accordance with embodiments of the present invention.

In these and other embodiments of the present invention, there are two main electronic topologies used to generate signal output. The first is that of a plain voltage divider as shown in FIG. 13. The force sensing resistor 114, 214, 314 may be thought of as a non-linear variable resistor R2, operable in response to applied load and therefore, signal output may be directly linked to its varying resistance. This output V2 will be non-linear, starting at a high (rail) level and dropping asymptotically to a low level. Circuit supply voltage V1 and passive resistors R1 work to define the operating limits of this curve.

Figure 14:
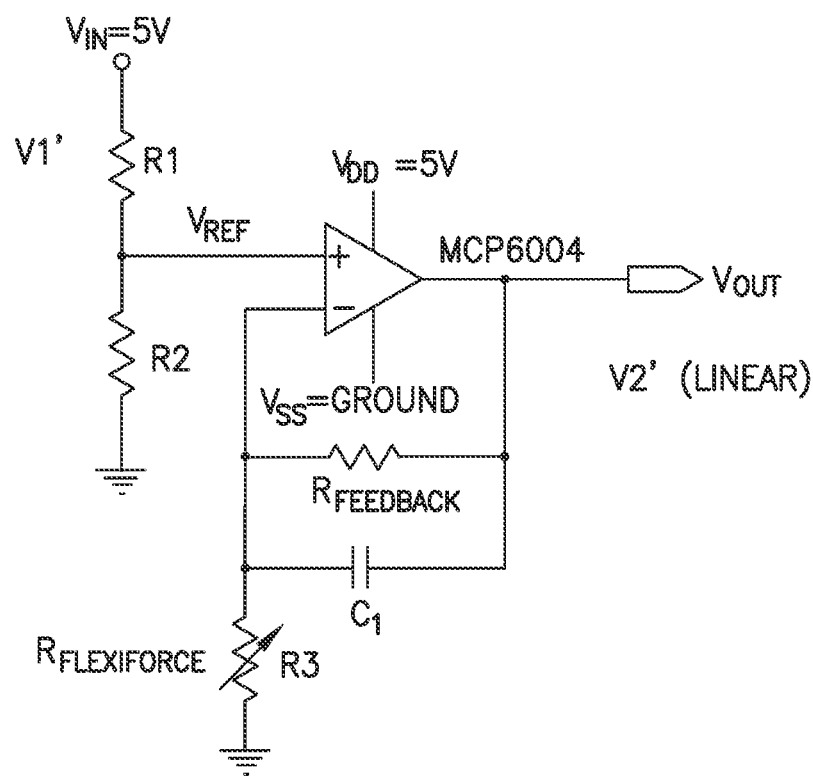
FIG. 14 is an exemplary op-amp schematic incorporating a force sensing resistor, in accordance with embodiments of the present invention.

A second electrical topology is one that uses op-amps to create a linear output as shown in FIG. 14. The force sensing resistor 114, 214, 314 again acts as a variable resistor R3, operable in response to applied load and therefore, signal output is directly linked to its varying resistance. The signal V1', then applied to an op-amp will create an output V2' that will be linear between a high (rail) level and a low level.

In the context of a low-volume indicator for a pumping system, the force sensing resistor may be used either upstream or downstream of the pump module. Upstream means that a force sensing resistor 414 is placed between a reservoir 420 and a pump 422 as shown in FIG. 4. Downstream means that a force sensing resistor 514 is placed between a pump 522 and the delivery end 524 of the device as shown in FIG. 5. FIG. 4 is a block diagram illustrating the force sensing resistor 414 placed between the reservoir 420 and pump 422, and FIG. 5 is a block diagram illustrating the force sensing resistor 514 placed between the pump 522 and delivery end 524 of the device, in accordance with embodiments of the present invention.

When the force sensing resistor is used "downstream" between the pump and the delivery end of the device, it is operated under positive pressure conditions. That is, as shown in FIG. 5, the pump 522 is providing positive pressure for fluid displacement. Tuning of the restriction characteristics at the delivery end 524 of the device is critical to sizing the output of the sensor including the force sensing resistor 514. When fluid is pushed through a restriction 526 at a certain flow rate, basic fluid dynamics (i.e., Bernoilli and Hagen Poiseuille) dictate that a certain pressure is required upstream of the restriction 526. For proper use of the force sensing resistor 514, it is important to ensure that all components are sized where the pressure required is compatible with the operating range of the sensor including the force sensing resistor 514.

Output tuning of the sensor including the force sensing resistor 514 may also be accomplished on the electronics side by changing passive resistors used in the drive circuit topologies as shown in FIGS. 13 and 14. In the case of a positive displacement pump 522, each pulse of the pump 522 corresponds to a pulse recorded by the sensor including the force sensing resistor 514. When the pump 522 is empty, or near empty, it is expected that the pressure levels will be affected in the form of reduced sensed output that will be processed by an algorithm (e.g., run by a processor in the delivery device employing the pump or by a remote or wired controller for the delivery device) to then give the empty or near-empty indication, depending on the degree of pressure level drop.

Figure 6:
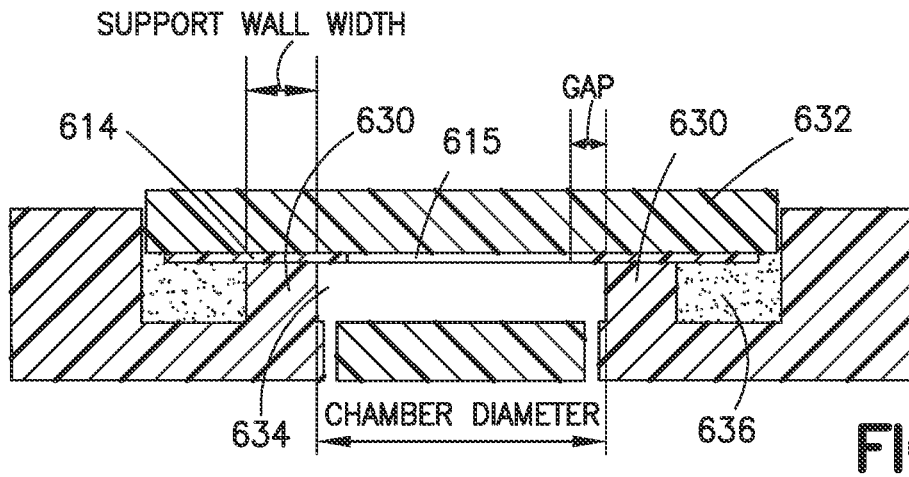
FIG. 6 is a cross-sectional view of an exemplary direct mode force sensing resistor operation, in accordance with embodiments of the present invention.
Figure 7:
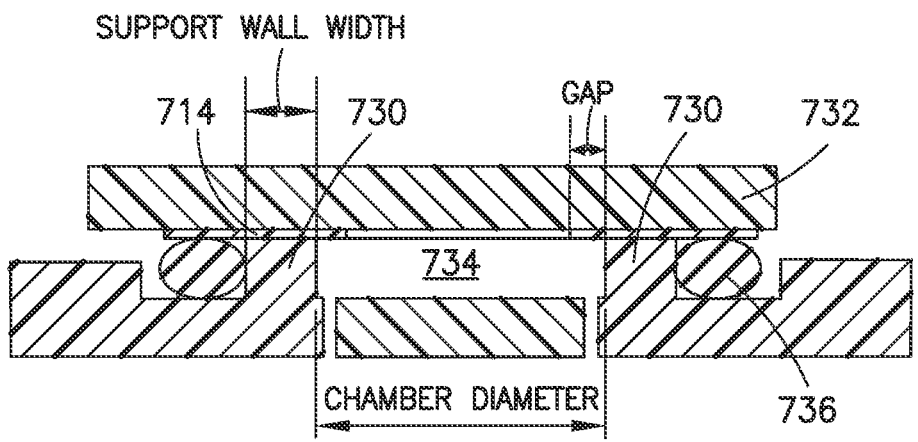
FIG. 7 is a cross-sectional view of another exemplary direct mode force sensing resistor operation, in accordance with embodiments of the present invention.
Figure 8:
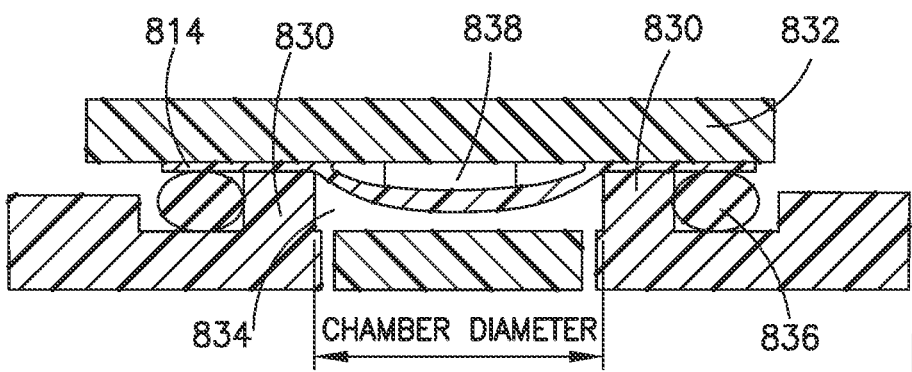
FIG. 8 is a cross-sectional view of another exemplary direct mode force sensing resistor operation, in accordance with embodiments of the present invention.

In the case of direct contact, the force sensing resistor is integrated in such a way that any pre-load of the force sensing resistor is minimized, so as not to affect its sensing dynamic range. In order to do so, the force sensing resistor is captured and held at a certain distance away from the force sensing resistor's critical sensing active area. Specifically, as shown in FIGS. 6, 7 and 8, a force sensing resistor 614, 714, 814 is captured by an annular wall 630, 730, 830 having a support wall width that is a certain gap distance away from the force sensing resistor's critical sensing active area. FIGS. 6, 7 and 8 are cross-sectional views of an exemplary direct mode force sensing resistor operation in accordance with illustrative embodiments of the present invention. A cover 632, 732, 832 is used to provide support, as well as to provide a means for clamping so that fluid is fully contained in the chamber 634, 734, 834 formed by the force sensing resistor 614, 714, 814 and the support structure, and having a diameter defined by the wall 630, 730, 830. It is to be understood that the sensing resistor 614, 714, 814 can be configured with different support structure defining a different chamber than the wall 630, 730, 830 and cover 632, 732, 832 arrangement to define a chamber 634, 734, 834. For example, as described below, the pressure or flow sensor can be mounted (e.g. heat staked or via adhesive) with respect to a fluid channel in a baseplate whereby the pressure or flow sensor is in direct contact with the fluid or indirect contact by way of a film or puck between the fluid path and the sensor. Alternatively, a chamber and sensor arrangement can be preassembled and connected at a pump inlet and/or outlet via tubing or other fluid path means.

A sealing material in the form of an o-ring/gasket 736, 836, either solid or soft/cured, is placed between the force sensing resistor 714, 814 edge and the supporting structure as shown in FIGS. 7 and 8. FIG. 7 illustrates a direct contact integration methodology using o-ring/gaskets 736 to seal the fluid chamber 734. In the embodiment of FIG. 7, the top cover 732 can be held in place using adhesives, mechanical clamping, welding (i.e., ultrasound, laser, and so forth). The embodiment of FIG. 7 can be used for example, in a downstream configuration where positive pressure levels are targeted.

FIG. 8 illustrates another direct contact integration methodology using o-ring/gaskets 836 to seal the fluid chamber 834 for use in an upstream configuration. In the embodiment of FIG. 8, the sensor output is pre-biased using a cover pre-load inducer 838 and sized to work with negative pressures that work to reduce the amount of mechanical bias on the sensor including the force sensing resistor 814.

FIG. 6 illustrates a general direct contact integration methodology where adhesive 636 is used to hold all parts and components in place. As an adhesive 636 is used to securely hold all parts and components in place, the embodiment of FIG. 6 can be used for example, in a downstream configuration where positive pressure levels are targeted.

When the force sensing resistor is used "upstream", between a reservoir and pump, it is typically operated under negative pressure conditions. Here the pump is pulling fluid from the reservoir by generating a lower pressure than is present in the reservoir chamber. This lower pressure creates a negative gradient in the flow channel that is translated all the way to the force sensing resistor. The force sensing resistor must therefore be integrated in a way that allows detection with a negative pressure, i.e. a pressure that wants to "pull" on the sensor face as opposed to pushing against the sensor face, as in the typical mode of use for a force sensing resistor.

Figure 10:
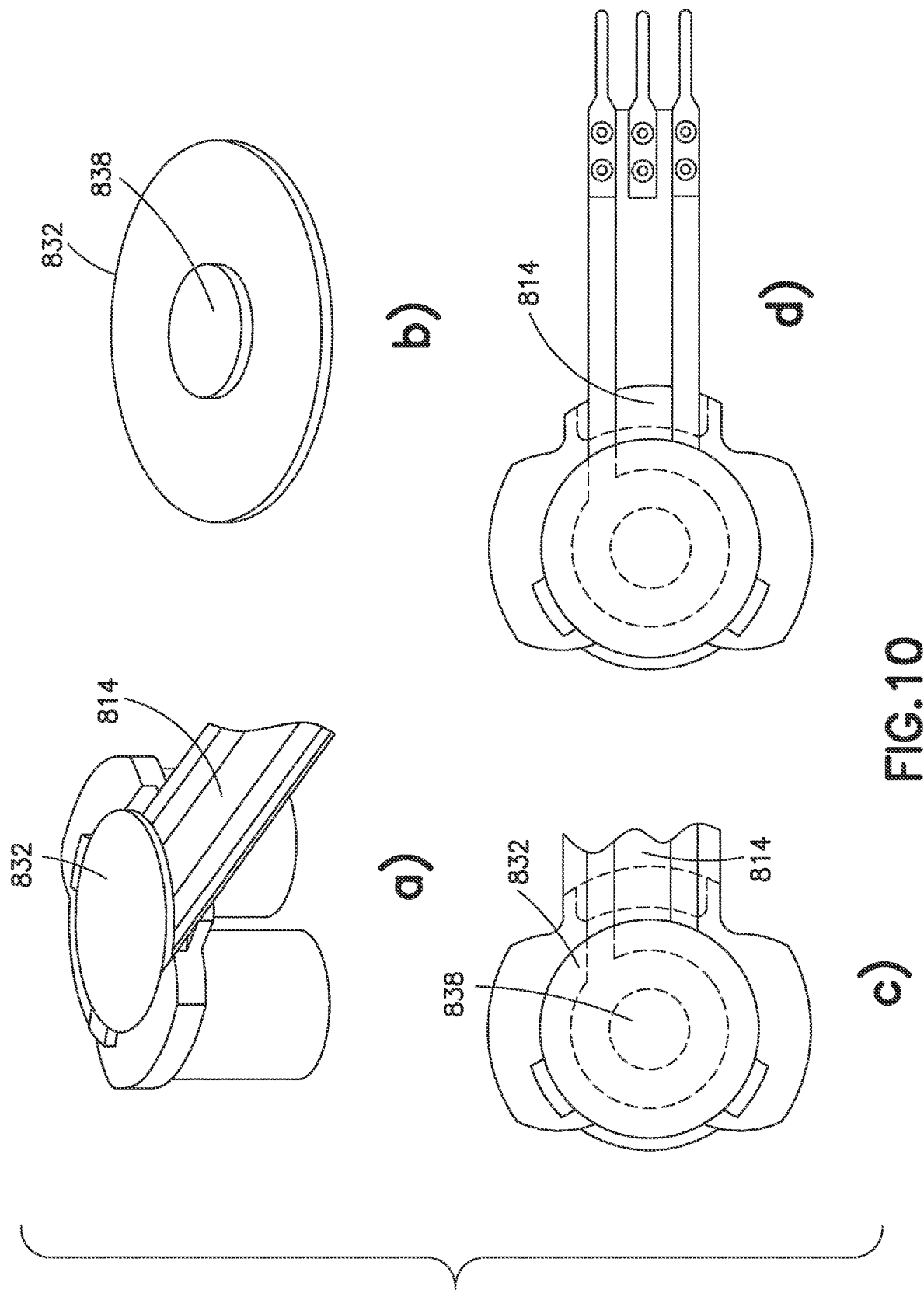
FIG. 10 are views (a), (b), (c) and (d) of a test-bed and force sensing resistor sensor constructed in accordance with illustrative embodiments of the present invention.

In accordance with an exemplary embodiment of the present invention, to sense negative pressures when the force sensing resistor is used "upstream", between a reservoir and pump, the device is staged to preload the sensor including the force sensing resistor in such a way that negative pressures in the fluid chamber work to reduce the pre-load. A method for pre-loading the sensor including the force sensing resistor is to capture it with a plate that includes a raised feature that "pushes" on the sensor including the force sensing resistor, thus creating a pre-load as shown in FIG. 8. In the embodiment of FIG. 8, the sensor output is pre-biased using a cover pre-load inducer 838 and sized to work with negative pressures that work to reduce the amount of mechanical bias on the sensor including the force sensing resistor 814. View (a) of FIG. 10 shows a test-bed for such an exemplary upstream sensing with a force sensing resistor 814 of FIG. 8, and view (b) of FIG. 10 shows the detail of exemplary pre-load features 838 on a cover 832 that supports the back of the force sensing resistor 814. View (c) is a view of an assembled test-bed, wherein the transparent portion includes the chamber 834 and connection posts for fluid connection, and view (d) illustrates a complete device.

Figure 9:
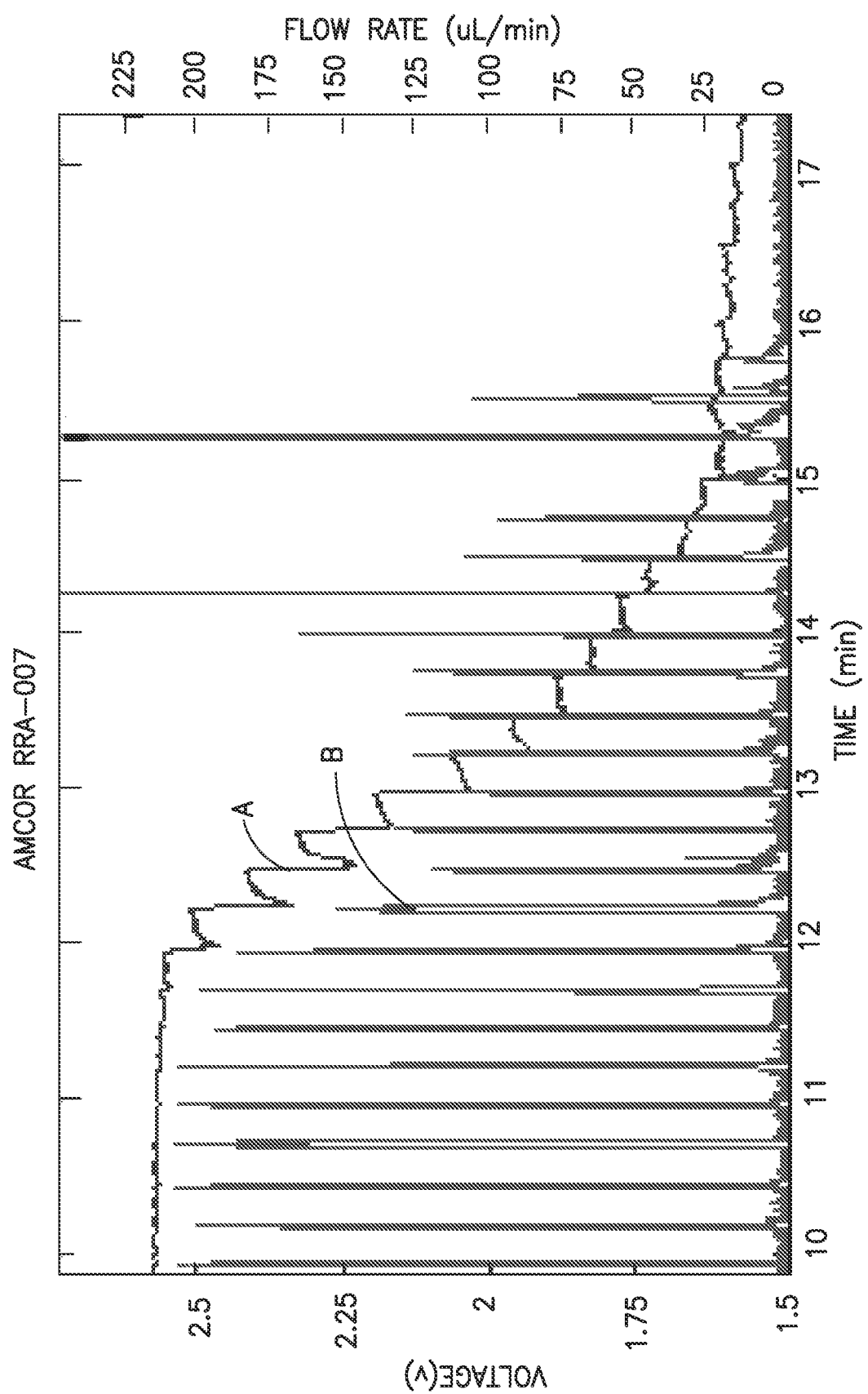
FIG. 9 is a representative plot of a force sensing resistor sensor output (line A) when used between the reservoir and pump of the device for low-volume detection, in accordance with embodiments of the present invention.

Low-volume detection is therefore accomplished by looking at the change in sensor including the force sensing resistor output that corresponds to a larger negative relative pressure generated in the upstream channel between a pump and a reservoir. An example of this behavior is shown in FIG. 9. FIG. 9 is a representative plot of a force sensing resistor sensor output (line A) when used upstream for low-volume detection. An output voltage V plotted on a left vertical axis, and a flow rate is plotted on an opposite vertical axis. Time increments are shown on the horizontal axis. The line A corresponds to the force sensing resistor output and the line B corresponds to the output of an in-line flow sensor showing reduced fluid flow that is related to a change in sensor output. As shown, as the flow rate drops due to low-volume, the force sensing resistor output drops in a similar manner, thereby indicating the irregular system condition specifically, the fluid low-volume.

The currently preferred embodiment is the "upstream" use of the sensor including the force sensing resistor, with a flexible, collapsible reservoir, where a direct correlation to the behavior of the emptying reservoir may be detected. In this configuration, as the collapsible reservoir nears empty, a distinct increase in negative relative pressure is observed. There are no comparable products/devices that provide such sensing at the price points available with the force sensing resistor-based solution. Indications from force sensing resistor vendors are that volume, relevant for a disposable medical device, pricing for force sensing resistor is in the range of $0.20-$0.50 each, thereby proving an effective and efficient device.

Second Embodiment: Occlusion Indicator

In the context of an occlusion indicator for a pumping system, the force sensing resistor is used downstream of the pump module. Downstream means that the force sensing resistor is placed between a pump and a delivery end of the device as shown in FIG. 5.

As noted above, in the case of direct contact, the force sensing resistor is integrated in such a way that any pre-load of the force sensing resistor is minimized, so as not to affect its sensing dynamic range. In order to do so, the force sensing resistor is captured and held at a certain distance away from the force sensing resistor's critical sensing active area. Specifically, as shown in FIGS. 6, 7 and 8, a force sensing resistor 614, 714, 814 is captured by an annular wall 630, 730, 830 having a support wall width that is a certain gap distance away from the force sensing resistor's critical sensing active area. FIGS. 6, 7 and 8 are cross-sectional views of exemplary direct mode force sensing resistor operation in accordance with embodiments of the present invention. A cover 632, 732, 832 is used to provide support, as well as to provide a means for clamping so that fluid is fully contained in the chamber 634, 734, 834 formed by the force sensing resistor 614, 714, 814 and the support structure, and having a diameter defined by the wall 630, 730, 830. As stated above, the sensing resistor 614, 714, 814 can be configured with different support structure defining a different chamber than the wall 630, 730, 830 and cover 632, 732, 832 arrangement to define a chamber 634, 734, 834.

A sealing material in the form of an o-ring/gasket 736, 836, either solid or soft/cured, is placed between the force sensing resistor 714, 814 edge and the supporting structure as shown in FIGS. 7 and 8. FIG. 7 illustrates a direct contact integration methodology using o-ring/gaskets 736 to seal the fluid chamber 734. In the embodiment of FIG. 7, the top cover 732 can be held in place using adhesives, mechanical clamping, welding (i.e., ultrasound, laser, and so forth). The embodiment of FIG. 7 can be used for example, in a downstream configuration where positive pressure levels are targeted When the force sensing resistor is used "downstream", between the pump and the delivery end of the device, it is operated under positive pressure conditions. That is, as shown in FIG. 5, the pump 522 is providing positive pressure for fluid displacement. Tuning of the restriction characteristics at the delivery end 524 of the device is critical to sizing the output of the sensor including the force sensing resistor 514. When fluid is pushed through a restriction 526 at a certain flow rate, basic fluid dynamics (i.e., Bernoilli and Hagen Poiseuille) dictate that a certain pressure is required upstream of the restriction 526. For proper use of the force sensing resistor 514, it is important to ensure that all components are sized where the pressure required is compatible with the operating range of the sensor including the force sensing resistor 514.

Figure 11:
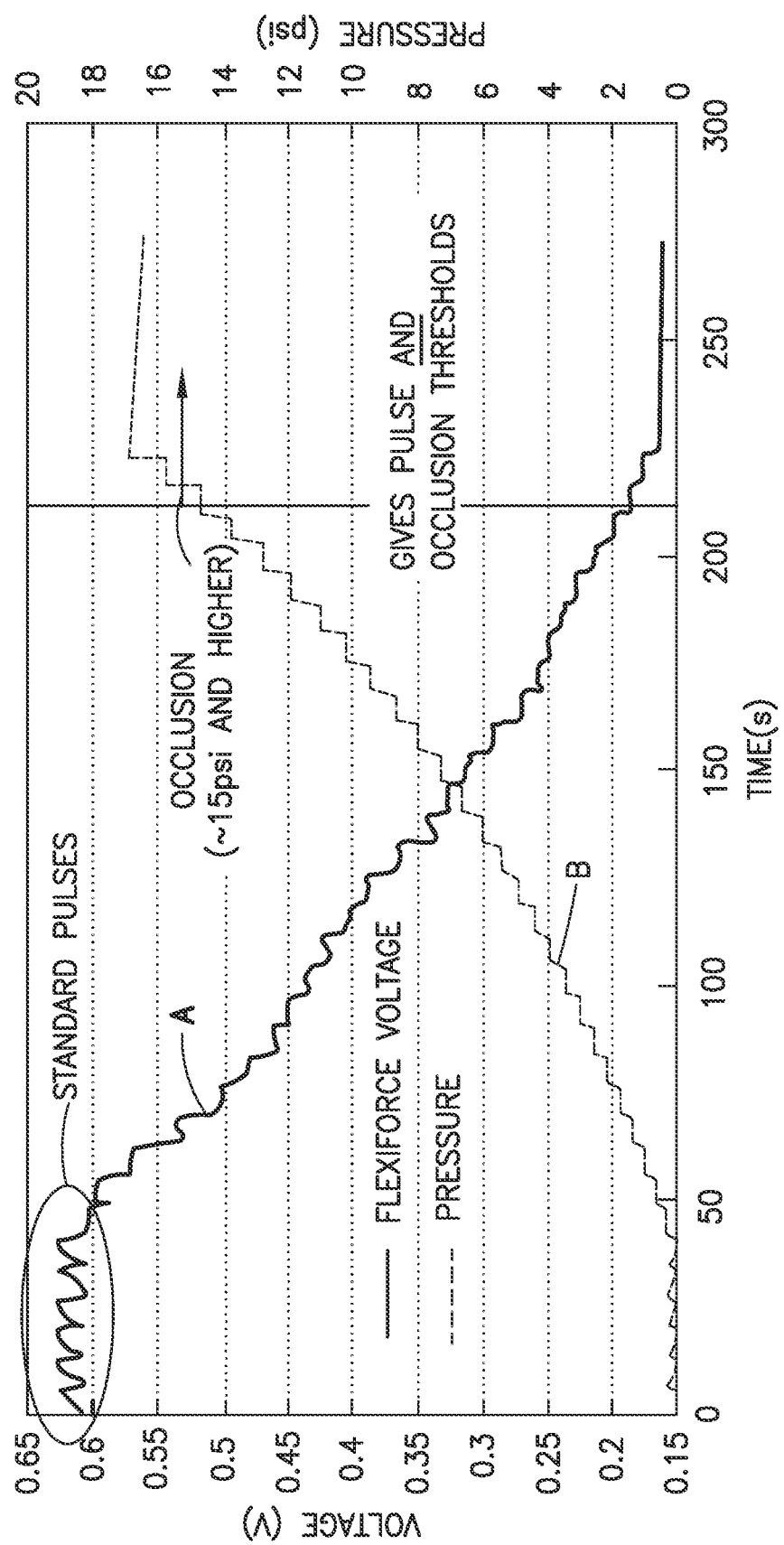
FIGS. 11 and 12 are representative plots illustrating a force sensing resistor based sensor output voltage and occlusion in accordance with embodiments of the present invention.
Figure 12:
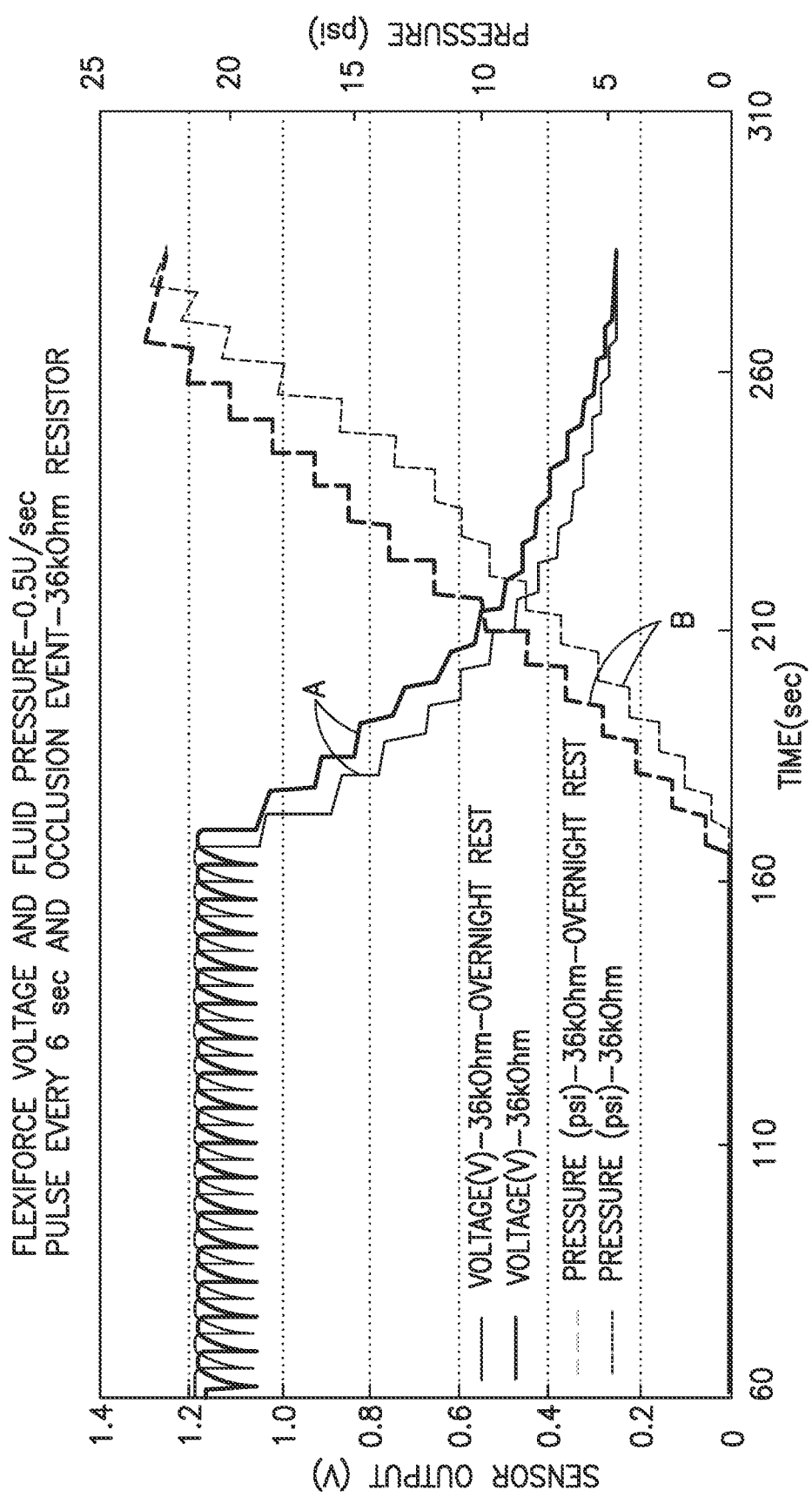

Output tuning of the sensor including the force sensing resistor 514 may also be accomplished on the electronics side by changing passive resistors used in the drive circuit topologies as shown in FIGS. 13 and 14. In the case of a positive displacement pump 522, each pulse of the pump 522 corresponds to a pulse recorded by the sensor including the force sensing resistor 514, and the sensor including the force sensing resistor 514 may be used to guarantee that the pump 522 is operating properly. More importantly, if there is a downstream occlusion, this will be recorded as a different sensor output with no decay, at least until the occlusion is removed. Depending on the drive circuit topology, the output may be increasing (i.e., op-amp topology) or decreasing (i.e., voltage divider topology). FIGS. 11 and 12 illustrate examples of a voltage divider test setup that demonstrates use in occlusion detection.

FIGS. 11 and 12 are plots illustrating sensor voltage (line A) and occlusion pressure (line B). An output voltage is plotted on a left vertical axis, and a pressure is plotted on an opposite vertical axis. Time increments are shown on the horizontal axis. The line A corresponds to the force sensing resistor output and the line B corresponds to the output of an in-line pressure sensor showing increased pressure that is related to a change in occlusion. As shown, as the pressure increases due to occlusion, the force sensing resistor output drops in a similar manner, thereby indicating the irregular system condition and specifically the occlusion.

As stated above, a need exists for an improved flow sensor that can operate in different types of fluid delivery mechanisms such as a pump for delivering a fluid medication including, but not limited to, insulin. To facilitate infusion therapy, there are generally two types of insulin pumps, namely, conventional pumps and patch pumps. Conventional pumps use a disposable component, typically referred to as an infusion set, tubing set or pump set, which conveys the insulin from a reservoir within the pump into the skin of the user. The infusion set includes a pump connector, a length of tubing, and a hub or base from which a cannula, in the form of a hollow metal infusion needle or flexible plastic catheter, extends. The base typically has an adhesive that retains the base on the skin surface during use. The cannula can be inserted onto the skin manually or with the aid of a manual or automatic insertion device. The insertion device may be a separate unit employed by the user.

Another type of insulin pump is a patch pump. Unlike a conventional infusion pump and infusion set combination, a patch pump is an integrated device that combines most or all of the fluidic components in a single housing. Generally, the housing is adhesively attached to an infusion site on the patient's skin, and does not require the use of a separate infusion or tubing set. A patch pump containing insulin adheres to the skin and delivers the insulin over a period of time via an integrated subcutaneous cannula. Some patch pumps may wirelessly communicate with a separate controller device (as in one device sold by Insulet Corporation under the brand name OmniPod®), while others are completely self-contained. Such patch pumps are replaced on a frequent basis, such as every three days, or when the insulin reservoir is exhausted. Otherwise, complications may occur, such as restriction in the cannula or the infusion site.

As patch pumps are designed to be a self-contained unit that is worn by the patient, preferably, the patch pump is small, so that it does not interfere with the activities of the user. The methods and apparatuses relating to flow sensing described herein in accordance with illustrative embodiments of the present invention are advantageous because they allow for flexibility and compactness when positioning a flow sensor upstream or downstream of a pump and therefore space efficiency within a device such as a patch device.

Figure 15:
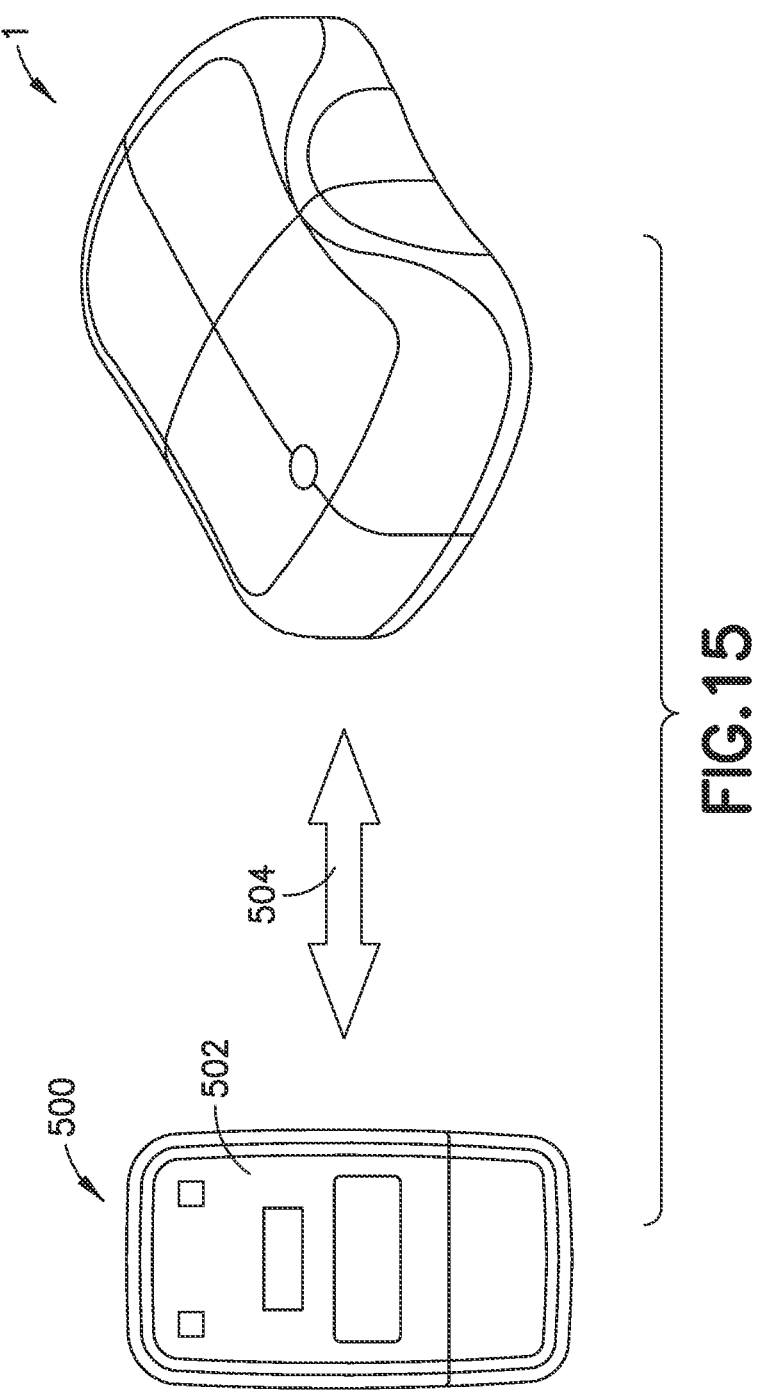
FIG. 15 illustrates an example wireless remote controller for controlling the operation of a medicine delivery device such as, for example, a patch pump, in accordance with an illustrative embodiment of the present invention.

With reference to FIG. 15, the wearable medical delivery device (e.g., insulin delivery device (IDD)) such as patch pump 1 is operable in conjunction with a remote controller that preferably communicates wirelessly with the pump 1 and is hereinafter referred to as the wireless controller (WC) 500. The WC can comprise a graphical user interface (GUI) display 502 for providing a user visual information about the operation of the patch pump 1 such as, for example, configuration settings, an indication when a wireless connection to the patch pump is successful, and a visual indication when a dose is being delivered, among other display operations. The GUI display 502 can include a touchscreen display that is programmed to allow a user to provide touch inputs such as a swipe to unlock, swipe to confirm a request to deliver a bolus, and selection of confirmation or settings buttons, among other user interface operations.

Figure 16:
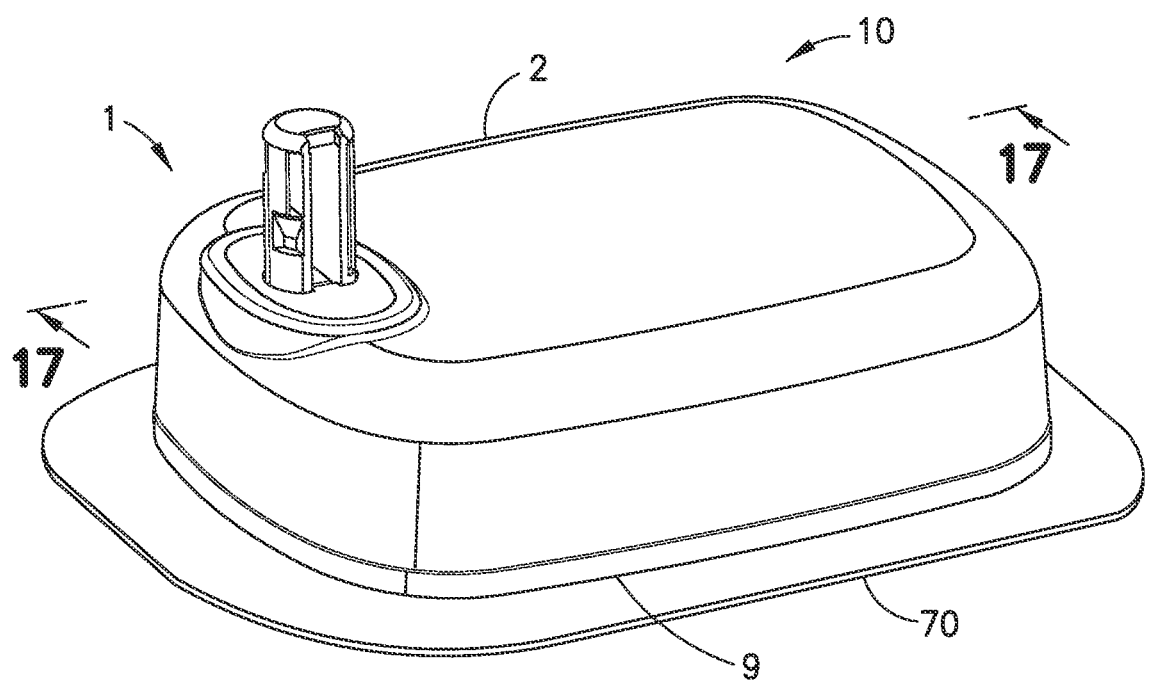
FIG. 16 is a perspective view of a patch pump in accordance with an illustrative embodiment of the present invention.

FIG. 16 is a perspective view of a patch pump 1 according to an illustrative embodiment of the present invention. The patch pump 1 has a housing 10, which includes a main cover 2 liquid sealed or, preferably, hermetically sealed to a base 9. The base 9 carries various components as described below. The hermetic seal prevents fluid ingress and prevents other particles from passing the seal. Embodiments of the patch pump 1 also include a vent or a vent membrane along with a sealing method described herein to provide pressure equalization. Embodiments of the seal include, for example, a liquid-tight seal, an O-ring seal or another mechanical seal, a gasket, an elastomer, a heat seal, an ultra-sonically welded seal, a laser weld, chemical joining, an adhesive, a solvent weld, or an adhesive weld. Laser welding is the preferred sealing method because, when laser welding is properly performed, a seamless fully hermetic seal is formed. The vent or the vent membrane continues to have the functional purpose of equalizing internal pressure and providing a sterile environment.

Figure 17:
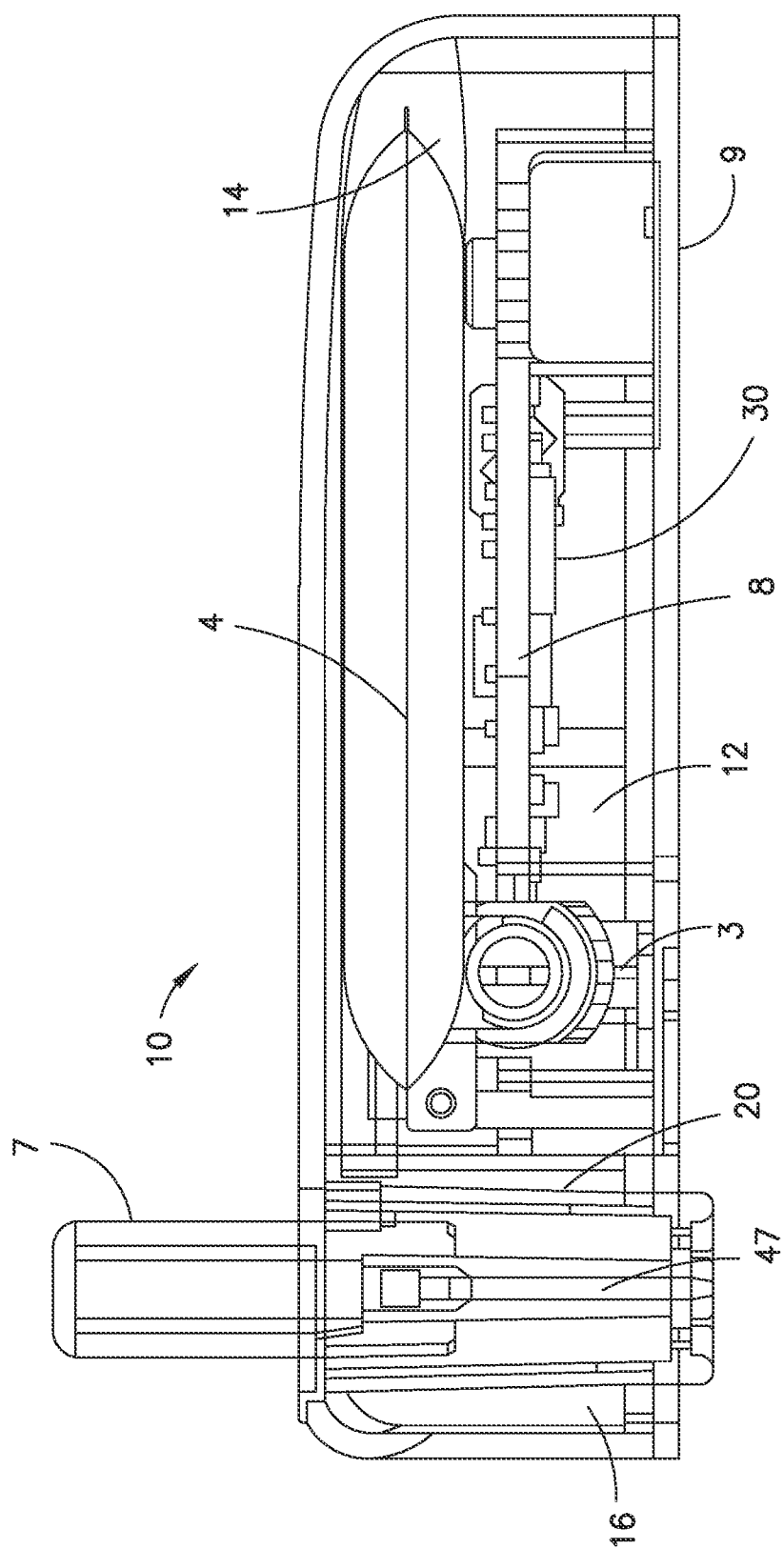
FIG. 17 is a cross-sectional view of FIG. 16 taken along line 17-17 of FIG. 16.

FIG. 17 is a cross-sectional view of the patch pump 1 illustrating various components. The main cover 2 and the base 9 define an interior 12 divided by a barrier 20 into a first internal region 14 and a second internal region 16. According to one embodiment, the patch pump 1 preferably includes a reservoir 4 for storing medicament (such as insulin), a pump 3 for pumping the medicament to exit the reservoir 4, and a sensor using a force sensing resistor or other sensor 30 for detecting an amount of pressure in a medicament flow path. The patch pump 1 also preferably includes electronics 8 for programming and operating the patch pump 1, and an insertion mechanism 7 for inserting a cannula 47 into a skin of the patient to deliver medicament.

As previously noted, the interior 12 of the patch pump 1 is divided by the barrier 20 into the first internal region 14 and the second internal region 16. According to one embodiment, the barrier 20 is a part of the main cover 2. Preferably, the barrier 20 is integrally formed as a unitary structure with the main cover 2. The barrier 20 is preferably sealed to a protrusion 18 on the base 9 such that the interface between the barrier 20 and the protrusion 18 is hermetically joined using any of the processing methods described above or any other appropriate conventional sealing method. Alternatively, the interface between the barrier 20 and the protrusion 18 can be liquid sealed. The barrier 20 separates the first internal region 14 from the second internal region 16 and protects the first internal region 14 from fluid ingress. According to one embodiment, the second internal region 16 is not sealed from fluid ingress.

The first internal region 14 includes components such as the pump 3, the sensor using a force sensing resistor or other pressure or flow sensor 30, and the electronics 8. Examples of the electronics 8 include semiconductor chips, controllers, diodes, antennas, coils, batteries, discrete components (resistors and capacitors, for example) and circuit boards used to operate and control the patch pump 1 and operate the pump 1 in conjunction with the WC 500. As readily understood by the skilled artisan, it is desirable to have a dry environment for proper operation of these components, particularly the electronics 8. The second internal region 16 includes the insertion mechanism 7 and the cannula 47. According to one embodiment, because the insertion mechanism 7 interfaces with the skin of a patient, the second internal region 16 is neither a hermetically sealed environment, nor a liquid-tight environment.

According to one embodiment, the components of the first internal region 14 are different from the components of the second internal region 16. Alternatively, the first internal region 14 and the second internal region 16 share some of the same components. For example, in some embodiments, portions of the reservoir 4 are disposed in both the first and second internal regions 14, 16. When the reservoir and the insertion mechanism 7 are separated by the barrier 20, however, the two internal regions 14, 16 fluidly communicate for effective operation of the patch pump 1.

Figure 18:
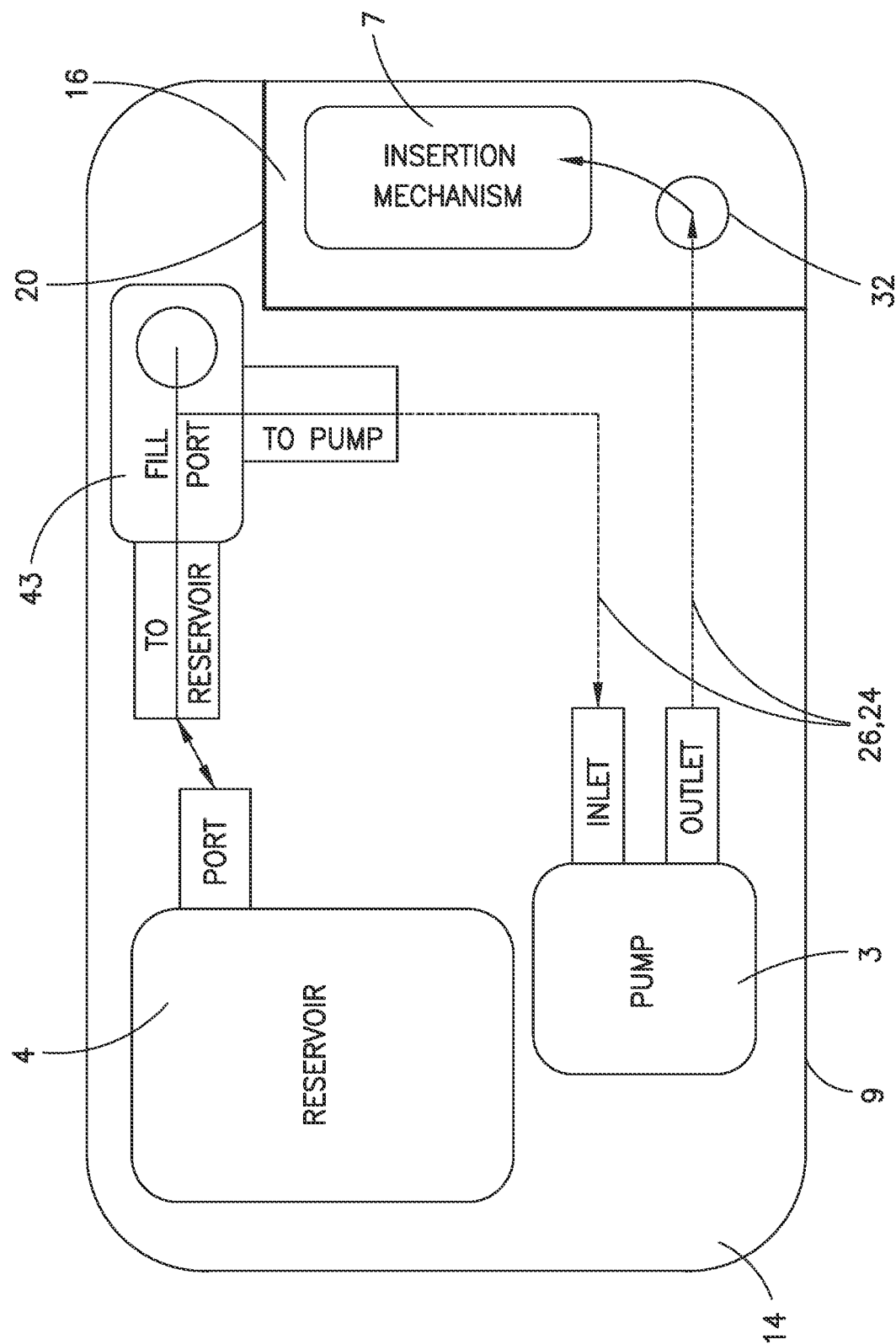
FIG. 18 is a schematic illustration of a medicament flow path of a patch pump and optional locations for flow sensing in accordance with an embodiment of the present invention.

FIG. 18 is a schematic of an exemplary fluid path in the patch pump 1 in accordance with an illustrative embodiment of the present invention. Medicament enters the patch pump 1 via the fill port 43 to fill the reservoir 4. During operation of the patch pump 1, the pump 3 pulls medicament to exit the reservoir 4 into the fill port 43 via an auxiliary port, and subsequently flow to the inlet of the pump 3 via the second fluid channel 26. Next, the pump 3 drives the medicament to exit the pump 3, enter the first fluid channel 24, and flow to the receptacle 32 of the insertion mechanism 7. Finally, the insertion mechanism 7 receives the medicament from the receptacle 32 via tubing, for example, and delivers the medicament through the cannula 47 to the skin of the patient.

Figure 19:
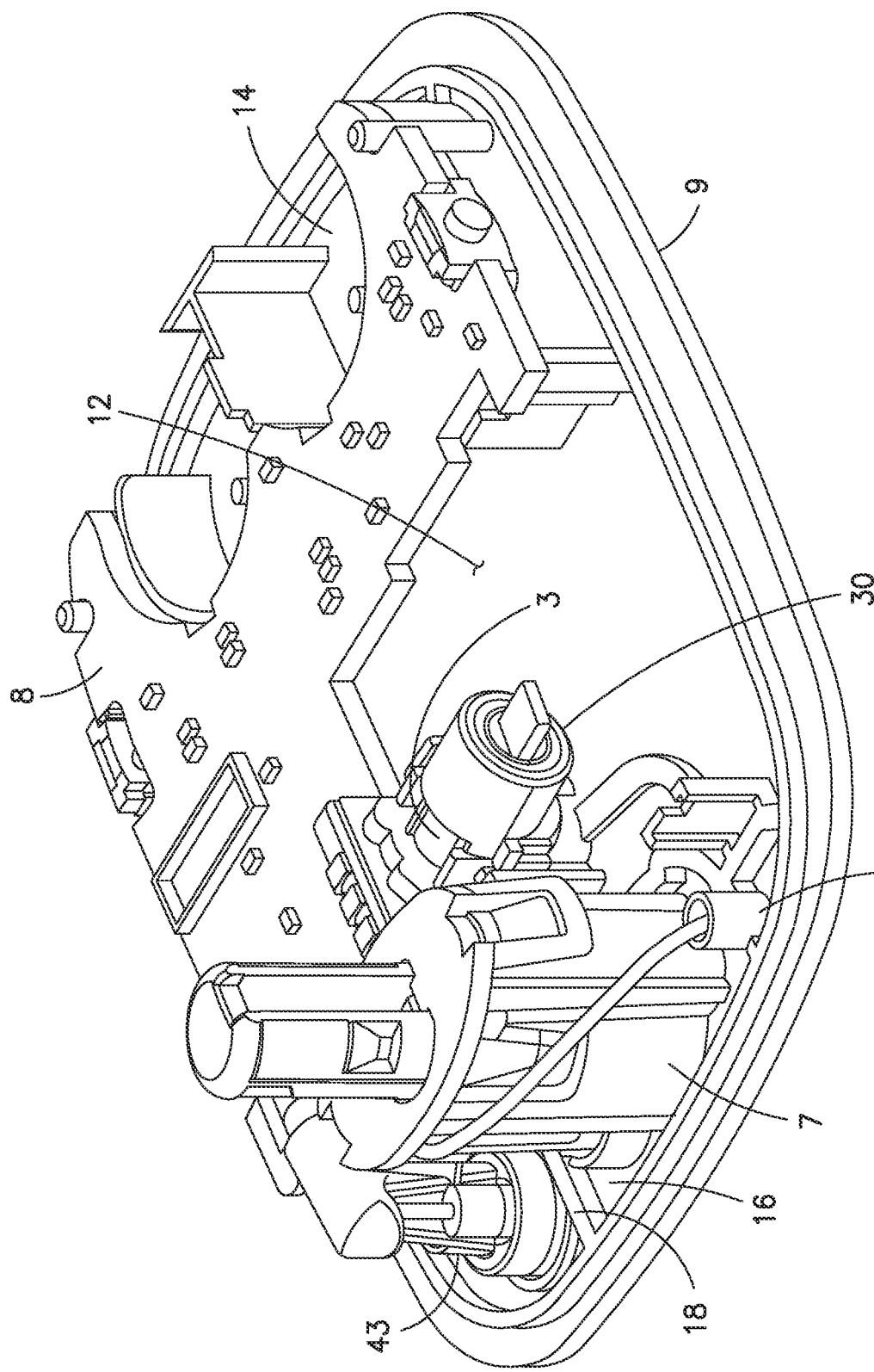
FIG. 19 is a perspective view of the patch pump of FIG. 16, omitting a cover and a reservoir.

FIG. 19 illustrates some of the main components of the patch pump 1 in a perspective view with the main cover 2 and the reservoir 4 removed for clarity. According to one embodiment, the fill port 43 is a conduit for supplying the medicament to the reservoir 4. The fill port 43 can be disposed in the first internal region 14 or the second internal region 16, but is preferably located in the first internal region 14. In some embodiments, the fill port 43 includes a portion that serves as part of the flow path for medicament exiting the reservoir 4.

Preferably, a receptacle 32 is connected to the insertion mechanism 7 by tubing, for example, to transfer the medicament to the insertion mechanism 7 prior to injection into the skin of the patient. According to one embodiment, the receptacle 32 is disposed in the second internal region 16.

Figure 20:
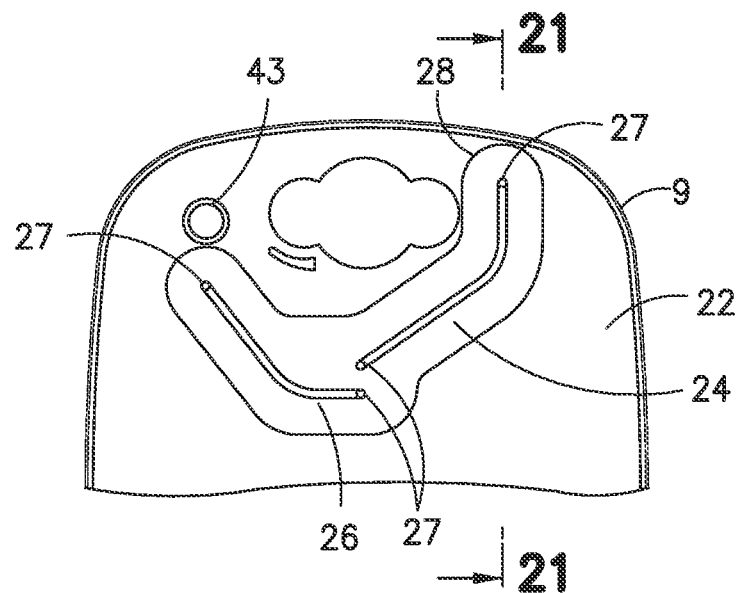
FIG. 20 is a partial bottom view of the patch pump of FIG. 16.

FIG. 20 illustrates a bottom surface 22 of the base 9 of the patch pump 1. During use, the bottom surface 22 is oriented toward the skin of the patient. In some embodiments, the bottom surface 22 can include adhesive that removably attaches the base 9 to the skin of the patient. Alternatively, an adhesive pad 70, as illustrated in FIG. 6, adheres to both the bottom surface 22 and the skin of the patient. Preferably, 3M™ medical tape (e.g. product no. 1776) is the adhesive used, although various types of known industry adhesives can be used. However, the adhesive is carefully selected to ensure compatibility with human skin to prevent undesired reactions. Also, compatibility of the adhesive and the insulin is considered in case that the adhesive and the insulin accidentally mix. The adhesive or adhesive pad are also placed over a fluid channel cover 28 covering first and second fluid channels 24, 26 which are described in detail below.

As shown in FIG. 20, the bottom surface 22 of the base 9 includes first and second fluid channels 24, 26. The first and second fluid channels 24, 26 provide fluid pathways between various components in the patch pump 1. According to one embodiment, the first and second fluid channels 24, 26 advantageously establish fluid communication between various components such as the reservoir 4, the fill port 43, the force sensing resistor 30, the pump 3, and the insertion mechanism 7.

Preferably, the first and second fluid channels 24, 26 are recessed from (or inscribed into) the bottom surface 22, and are formed through a molding process, such as injection molding, or by a cutting process, such as milling. In other embodiments, the first and second fluid channels 24, 26 are disposed on the main cover 2, or on the base 9 within the interior 12 of the patch pump 1. Similar fluid channels can be positioned in a plurality of locations in embodiments of the device. As described herein, one or more flow or pressure sensors can be provided in the IDD 1 relative to a fluid channel 24 and/or 26 for convenient access to the fluid channel, the pump (e.g., upstream or downstream), and the electronics 8 needed to receive and process outputs from the sensor and optionally provide power to the sensor(s) 30.

The cross-sectional shape of the first and second fluid channels 24, 26 is defined based on desired flow characteristics. The geometry of the first and second flow channels 24, 26 is selected based on factors such as cost, manufacturing capability, and desired use. Exemplary cross-sectional profiles of the first and second fluid channels 24, 26 include square, rectangular, and semi-circular. One skilled in the art will appreciate that other cross-sectional profiles can be employed without departing from the scope of the present invention.

Preferably, the first and second fluid channels 24, 26 are sized to allow unrestricted medicament fluid flow. In other words, the pump 3 connected to the first and second fluid channels 24, 26 controls and determines the medicament fluid flow rate, instead of the size of the first and second fluid channels 24, 26. Specifically, if the first and second fluid channels 24, 26 are too small, capillary action can occur, potentially resulting in the obstruction of medicament fluid flow. Preferably, the cross-sectional area of the first and second fluid channels 24, 26 is greater than the gage of the cannula 47.

According to one embodiment as illustrated in FIG. 20, the first and second fluid channels 24, 26 are encapsulated by a fluid channel cover 28 which is illustrated as being transparent for clarity. But one skilled in the art will appreciate that the opacity of the fluid channel cover 28 or other portions of the device can vary without departing from the scope of the present invention. The fluid channel cover 28 is, for example, clear film, foil, a flexible sheet/film or a semi-rigid/rigid part made of any suitable material.

According on one embodiment, the film channel cover 28 is made of foil available from Oliver-Tolas Healthcare Packaging (e.g., TPC-0777A foil). Preferably, the film channel cover 28 is made of Oliver-Tolas Healthcare Packaging IDT-6187 clear film and is heat sealed or heat staked to the bottom surface 22 of the base 9 to embed the first and second fluid channels 24, 26. Laser welding, for example, applies laser light through the clear film to fix the film channel cover 28 to the bottom surface 22 of the base 9. Laser welding is advantageous because a laser can straddle the channel edge of the fluid channels 24, 26 during the welding process and adhere the film to the base 9 in areas that are closer to the channel edges than other methods.

The fluid channel cover 28 is sealed to the base 9 via any of the processing methods described above. Accordingly, it is desirable for the material of the fluid channel cover 28 to be compatible with the material of the base 9 for the purposes of effective processing, joining, liquid sealing, and hermetic sealing. In addition, because the medicament comes into contact with the fluid channel cover 28, care is taken in the selection of the fluid channel cover 28 to ensure compatibility with the medicament.

The sealed fluid channel cover 28 encloses and protects the medicament from any contamination while travelling through the first and second fluid channels 24, 26. According to one embodiment, a single fluid channel cover 28 encapsulates each of the first and second fluid channels 24, 26. Alternatively, a separate fluid channel cover 28 can encapsulate each of the first and second fluid channels 24, 26. Because fluid channels can also be disposed in the interior 12 of the patch pump 1 as described herein, one or more fluid channel covers 28 can be appropriately disposed in the interior 12 of the patch pump 1 as well.

Figure 21:
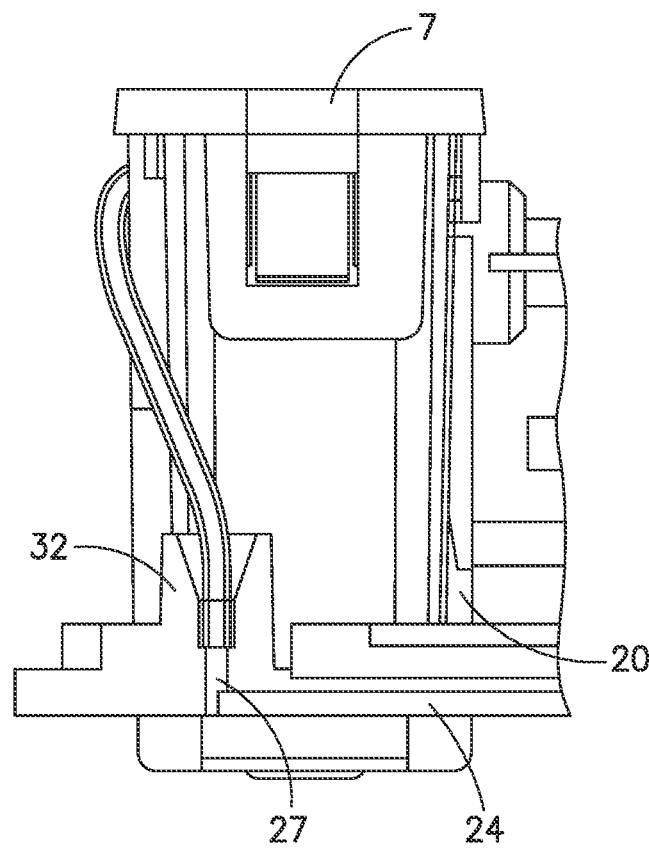
FIG. 21 is a partial cross-sectional view of the patch pump of FIG. 16 taken along line 21-21 of FIG. 20.

FIG. 21 is a partial cross-sectional view of the patch pump 1 of FIG. 16. According to one embodiment, the base 9 includes a fluid channel passageway 27, such as a through hole 27, which extends through the base 9. As shown in FIG. 10, the fluid channel passageway 27 advantageously connects the receptacle 32 to a first end of the first fluid channel 24. According to one embodiment, a fluid channel passageway 27 is similarly present at each end of the first and second fluid channels 24, 26 (see FIG. 9). Preferably, the fluid channel passageway 27 disposed in the base 9 at a second end of the first fluid channel 24 connects directly to the pump 3 disposed in the first internal region 14. Similarly, in a preferred embodiment, opposing ends of the second fluid channel 26 connect the reservoir fill port 43 and the pump 3 via the fluid channel passageways 27. A flow or pressure sensor can be provided, for example, in the internal region 16 where the insertion mechanism 7 is disposed. The sensor can be provided in or adjacent to a chamber into which the fluid flows, and the chamber can be mounted to the passageway 27 or to the tubing connecting the insertion mechanism to the passageway.

According to one embodiment, the medicament exits the first internal region 14 of the patch pump 1 via the passageway 27 in the base 9, entering the first fluid channel 24 in the bottom surface 22 outside of the interior 12 of the patch pump 1. Subsequently, via the fluid channel passageway 27 disposed at the first end of the first fluid channel 24, the medicament reenters the interior 12 of the patch pump 1 into the second internal region 16. By routing the medicament through the first fluid channel 24 outside the interior 12 of the patch pump 1, the first fluid channel 24 advantageously and effectively bypasses the barrier 20. Therefore, the first fluid channel establishes fluid communication between the pump 3 and the cannula 47 while bypassing the barrier 20, thereby maintaining the barrier 20 integrity. Thus, the first fluid channel 24 advantageously provides fluid communication between the first internal region 14, which is sealed from fluid ingress, and the second internal region 16, which is not sealed from fluid ingress without compromising the integrity of the barrier 20.

The configuration of the first and second fluid channels 24, 26 in the patch pump 1 provides a plurality of exemplary benefits. Because the first and second fluid channels 24, 26 are integral to the base 9, they are conveniently manufactured through molding and/or milling, thereby potentially reducing manufacturing costs. Additionally, the barrier 20 provides an effective seal between the first and second internal regions 14, 16 because the first and second fluid channels 24, 26 bypass the barrier 20 instead of penetrating the barrier 20. Such a sealing configuration advantageously ensures that the critical components in the first internal region 14 do not fail due to fluid ingress. The critical components are disposed in preferred locations, which provides for optimal component arrangement. Thus, the use of first and second fluid channels 24, 26 outside of the interior 12 of the patch pump 1 provides configurational freedom to designers, aids optimization of the interior space, and aids reduction of the overall size of the patch pump 1.

Figure 22:
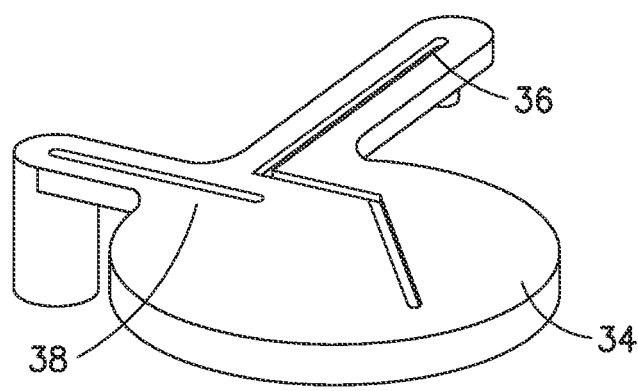
FIG. 22 is a perspective view of a fluid channel plate in accordance with an embodiment of the present invention.
Figure 23:
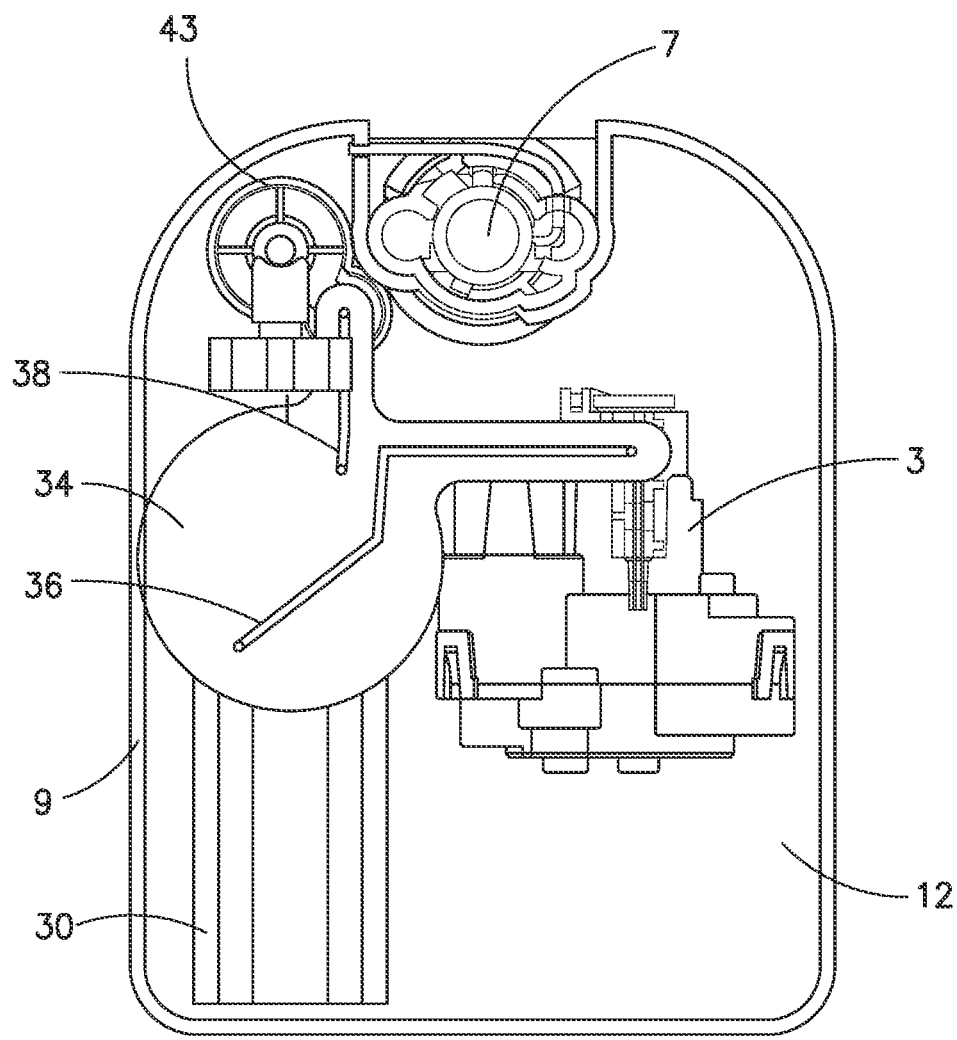
FIG. 23 is a top view of a patch pump incorporating the plate of FIG. 22 and omitting a cover and reservoir for clarity.

In an alternative illustrative embodiment of the present invention, as illustrated in FIGS. 22 and 23, a flow channel plate 34 is disposed in the interior 12 of the patch pump 1 to provide a medicament fluid pathway. The flow channel plate 34 includes first and second plate fluid channels 36, 38, encapsulated by a fluid channel cover 28, which is omitted for clarity. The plate fluid channels 36, 38 route medicament fluid flow to the various components through the interior 12 of the patch pump 1. As described herein, a pressure or flow sensor can be mounted on the flow channel plate 34 opposite the fluid channel cover 28 so as not to be in contact with the fluid, which can simplify design of the IDD 1 and regulatory approval by obviating the design issue of biocompatibility between the sensor and the fluid when in direct contact.

According to one embodiment, the sensor using the force sensing resistor or other sensor 30 is integrally formed into the flow channel plate 34 for in-line pressure sensing of the medicament fluid flow path. One embodiment of a flow channel plate 34 incorporates a receptacle to replace the fill port 43. Ports, receptacles, or joints can advantageously be included in the flow channel plate 34 to mate various components via a fluid path. According to one embodiment, the flow channel plate 34 is entirely disposed in the first internal region 14.

The medicament flow path in the flow channel plate 34 offers further flexibility and space optimization options for the arrangement of the various components in the patch pump 1. FIG. 23 illustrates an exemplary embodiment in which components at various locations in the patch pump 1 establish fluid communication via the first and second plate fluid channels 36, 38 in the flow channel plate 34. According to one embodiment, the first and second plate fluid channels 36, 38 in the flow channel plate 34 cooperate with the first and second fluid channels 24, 26 in the base 9 to provide fluid communication from the reservoir 4 to the insertion mechanism 7. As shown in FIG. 23, the pressure or flow sensor 30 is configured as a sensor that uses a force sensing resistor (e.g. sensor 314 in FIG. 3, sensor 814 in FIG. 10) connected adjacent to a fluid channel passageway 27 or other fluid channel in the flow channel plate 34 or base 9.

Figure 24:
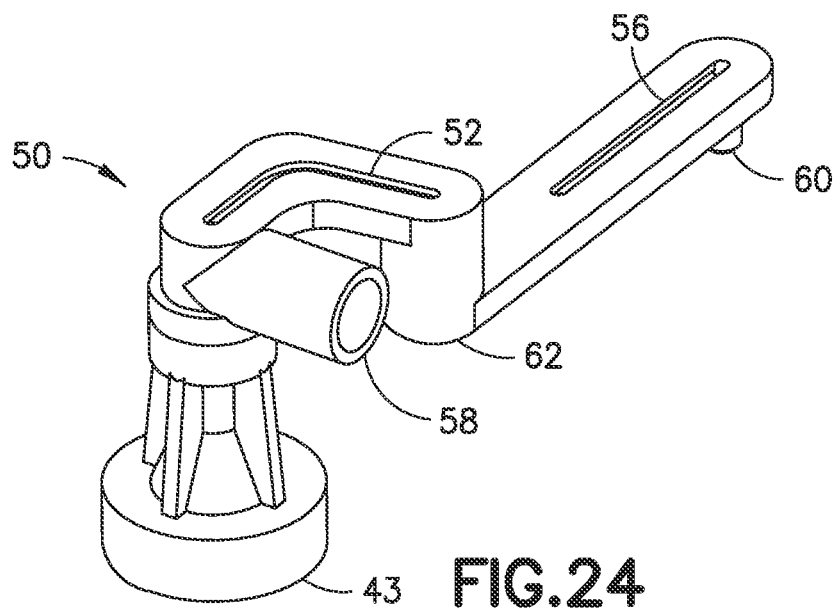
FIGS. 24, 25 and 26 are perspective views of a flow channel member in accordance with another embodiment of the present invention.
Figure 25:
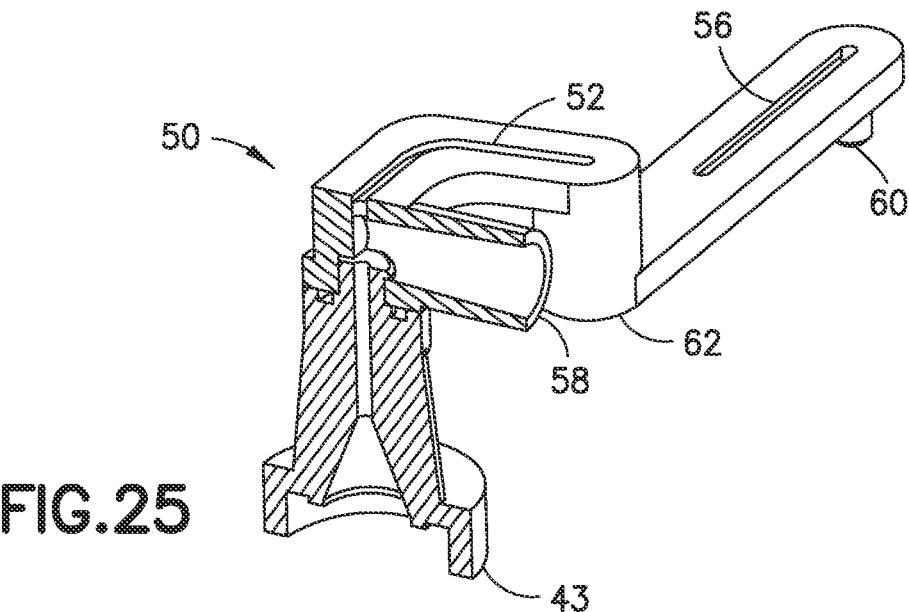
Figure 26:
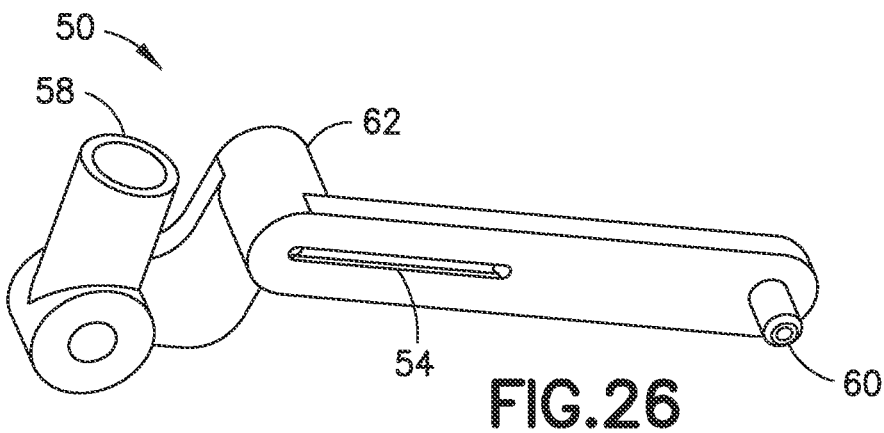

In another alternate embodiment, as illustrated in FIGS. 24, 25 and 26, a flow channel member 50 includes a first fluid channel portion 52, a second fluid channel portion 54, and a third fluid channel portion 56 at different elevations with respect to the fill port 43. The embedded first, second, and third fluid channel portions 52, 54, 56 route medicament fluid flow in different plane locations, as further described below. A pressure sensor or flow sensor can be disposed adjacent any one of the fluid channel portions 52, 54 and 56.

Specifically, a septum (not shown) is pierced to allow medicament to flow from the fill port 43 shown in FIGS. 24 and 25. For example, a user inserts a syringe (not shown) to pierce the septum in the fill port 43 to inject the medicament inside the flow channel member 50 to a first port 58. The first port 58 includes a first passageway and a second passageway. The first passageway connects the fill port 43 to the reservoir (not shown) to fill the reservoir 4. The second passageway connects the reservoir to the first fluid channel portion 52.

Prior to the pumping operation, the flow channel member 50 is in a closed system with the pump 3 (not shown) being in a closed chamber and connected at a second port 60. Fluid enters the flow channel member 50 and travels to the pump 3 and the reservoir 4 thereby filling each of the first, second and third fluid channel portions 52, 54, 56. Subsequently, fluid can enter and fill the reservoir 4. As the reservoir 4 is being filled, the flow channel member 50 is primed by driving the fluid through the flow channel member 50 by the pump 3 over several cycles to remove any air present.

During the pumping operation, medicament is drawn from the reservoir by the pump 3 (not shown) that is connected at the second port 60 disposed at the other end of the flow channel member 50. When the pump 3 generates a suctioning pressure, medicament is pulled from the reservoir into the first fluid channel portion 52 on a top surface of the flow channel member 50. The medicament subsequently flows down a junction 62 (e.g. a through hole) of the flow channel member 50 and enters into a second fluid channel portion 54 disposed on a bottom surface of the flow channel member 50. The second fluid channel portion 54 is in fluid communication with the third fluid channel portion 56.

According to one embodiment, a through hole connects the second and third fluid channel portions 54, 56. According to another embodiment, each of the second and third fluid channel portions 54, 56 is deeper than one-half the thickness of the flow channel member 50, and adjacent ends of the second and third fluid channel portions 54, 56 overlap to establish fluid communication therebetween. Thus, the medicament flows from the second fluid channel portion 54 to the end of the third fluid channel portion 56 where a second port 60 connects to the pump 3.

As described above, FIGS. 24 and 25 illustrate the first fluid channel portion 52 and the third fluid channel portion 56 being disposed on a top surface of the flow channel member 50 and FIG. 26 illustrates the second fluid channel portion 54 being disposed on a bottom surface of the flow channel member 50. In this exemplary embodiment, the flow channel member 50 has three separate fluid channel covers 28 (not illustrated for clarity) encapsulating each of the first, second, and third fluid channel portions 52, 54, 56. A pressure or flow sensor 30 can be disposed adjacent and in contact with the cover 28 and therefore need not be in the flow channel and in contact with the fluid.

The flow channel member 50, or the like, advantageously provides for a variety of different component arrangements in the patch pump 1 to establish fluid communication through the interior of the patch pump 1. Specifically, the flow channel member 50 advantageously provides different fluid channel portions 52, 54, 56 at different elevations or different planar positions to provide flexibility when interfacing the medicament flow path with the various components in the patch pump 1. The use of the flow channel member 50, or the like, with fluid paths at different elevations also advantageously provides alternate routing capabilities for space optimization within the patch pump interior 12.

Figure 27:
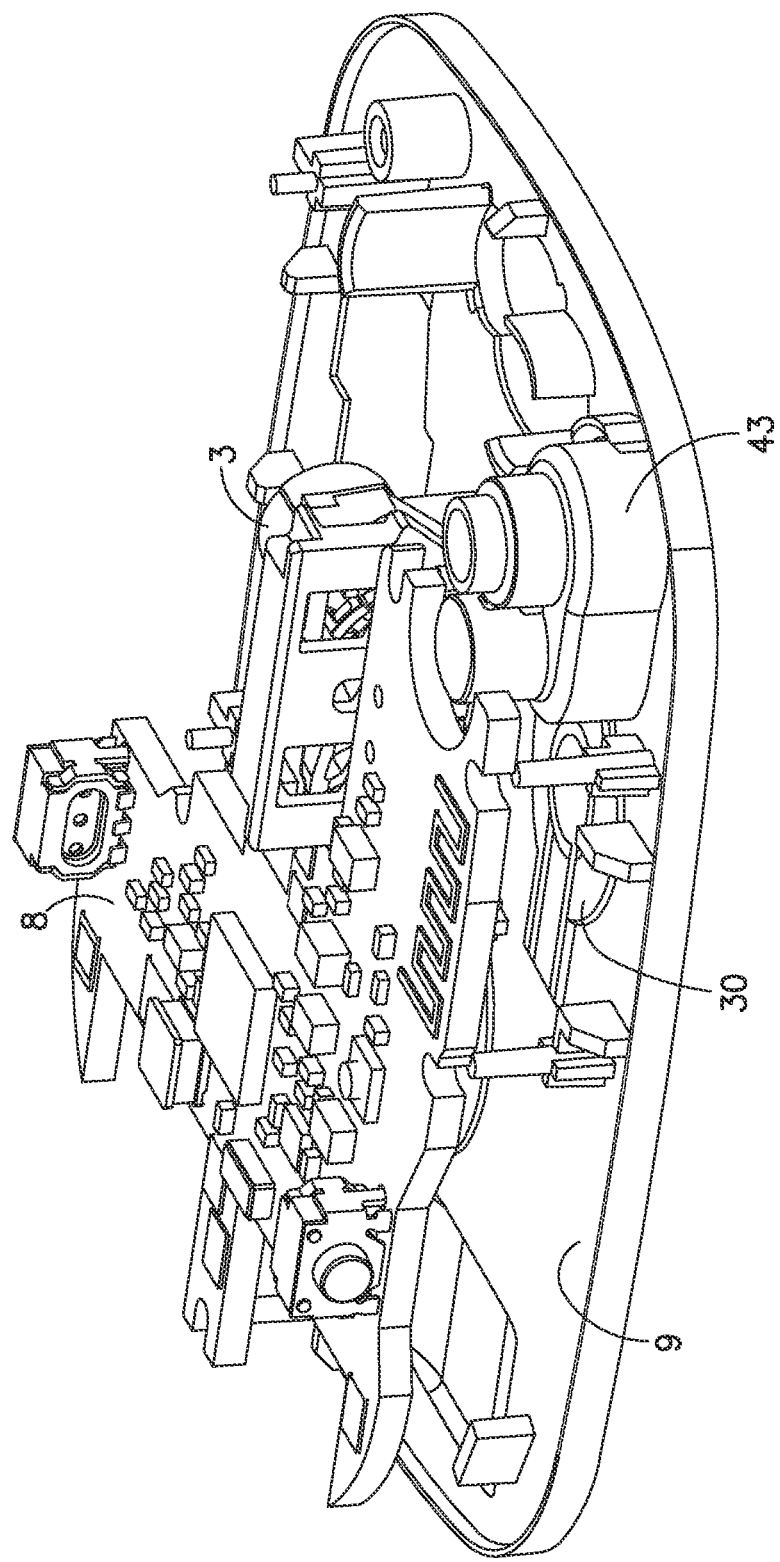
FIG. 27 is a perspective and partially exploded view of a pump employing a force sensing resistor-type sensor in accordance with another embodiment of the present invention.

In accordance with another illustrative embodiment of the present invention, a patch pump 1 is configured with a pressure sensor 30 such as a force sensing resistor-type sensor (e.g., sensor 314 in FIG. 3, or sensor 814 in FIG. 10(*d*)). FIGS. 27, 28 and 29 illustrate some of the main components of a patch pump 1 in a perspective view with the main cover 2 and the reservoir 4 removed for clarity. The main components depicted in FIG. 27 are electronics on a printed circuit board (PCB) 8, base 9, pump 3, fill port 43 and a sensor 30 comprising a force sensing resistor, for example. FIG. 27 is a slightly exploded view showing the electronics PCB 8 separated from the sensor 30 clarity. FIGS. 28 and 29 are top and bottom views of the base 9. The cover 28 for the fluid channels 24 and 26 has been removed from the bottom of the base 9 for clarity.

By way of an example, a portion 26' of the fluid channel 26 is exposed and therefore accessible to a sensor 30 from the top of the planar base 9. FIGS. 32A and 32B are respective cross-sections of the base 9 taken along the lines shown in FIG. 29. The portion 26' of the channel 26 is dimensioned to give sufficient access to the channel 26 for the desired type of sensing (e.g., a time of flight sensor may need a longer section of the path 26 than another type of pressure or flow sensor) and access for mounting of the sensing surface of the sensor. It is to be understood that the sensing surface of the sensor 30 can be seated within the portion 26' or a sensing cavity can be created by placing a sensor base or raised portion on top of the base 9 and over the exposed portion 26'.

The base 9 in the illustrative embodiment of FIG. 28 has a raised portion 29 that creates a sensing cavity 29' in which a sensor 30 or at least a sensing portion of the sensor 30 can be seated. The portion of the sensor 30 surrounding the sensing area seated in the cavity 29' can be adhered or otherwise mounted to the raised portion 29 of the base 9 (e.g., using adhesive, being heat staked, or held in place with gaskets and other mechanical mounting means) to create a seal that prevents fluid from leaking out of the fluid channel 24 and the sensing cavity 29' and into the interior 12 of the pump.

The sensing cavity 29' is dimensioned with a selected depth to avoid collapsing of the chamber or sensing area of a force sensing resistor-type sensor. In addition, the dimensions of the sensing cavity are selected to a desired amount of sensitivity to detect minimal pressure changes, as well as to minimize residual or dead volume of fluid in the sensing cavity 29'. As fluid flows in the fluid channels of the pump (e.g., channels 24 and 26 and other fluid paths within the pump 1), fluid in the cavity 29' contacts the exterior of the sensor 30 and pressure is determined from changes in pressure on the surface of the force sensing resistor sensor. The sensor 30 is electrically connected to the PCB 8 to provide sensed pressure data to a processor circuit on the PCB 8 and receive power as necessary. The sensor can be electrically connected to the PCB 8 by using a z-axis or vertical connector between conductive pad(s) or trace(s) on the sensor 30 and a corresponding conductive pad(s) or trace(s) on the PCB 8. The conductor between these pads or traces on the sensor 30 and PCB 8 can be, but are not limited to, a spring, a flexure (e.g., composed of spring steel or beryllium copper), a pogo pin connector, and a z-axis connector, for example. The flexible tail of the force sensing resistor-type sensor 30 (e.g., see 814 in FIG. 10(*d*)) can also be curved toward the PCB 8 and connected thereto via a zif connector. The force sensing resistor-type sensor comprises pressure sensing material enclosed between two sheets of plastic that is biocompatible with the fluid in the sensing cavity 29'.

The arrangement of the flow sensor 30 in FIG. 27 with respect to the fluid channel 26 is an upstream configuration whereby flow sensing is performed at a location along the IDD's fluid path that is before the fluid reaches the inlet of the pump. A sensor 30 can also be placed in a downstream configuration relative to the fluid channel 24 between the pump outlet and the delivery mechanism 47, for example. An advantage of using embedded fluid channels (e.g., channels 24 and 26) in the base 9 is that the length and route of the fluid channel can be easily altered when fluid channels are milled into the base 9 to accommodate a sensor 30 or other new components into the constraints of an existing layout of major components (e.g., pump 3, PCB 8, insertion mechanism 47, fill port 43, reservoir 4) in a patch pump 1 design. In the patch pump depicted in FIG. 27, for example, the route of the fluid channel 24 may need to be longer and more circuitous to allow sufficient room for a downstream pressure or flow sensor 30 to have access to an exposed portion of the channel 24 from the top of the base 9, along with accommodating the physical dimensions of the sensor and associated electronics and its connections to the PCB 8. In the case of a thermal time of flight-type of sensor 30, a longer sensing cavity 29' may be needed for access to a selected length of a straight portion of the fluid channel 24, 26 to retain the sensor functionality, as described below in connection with FIGS. 28A and 33.

Figure 30:
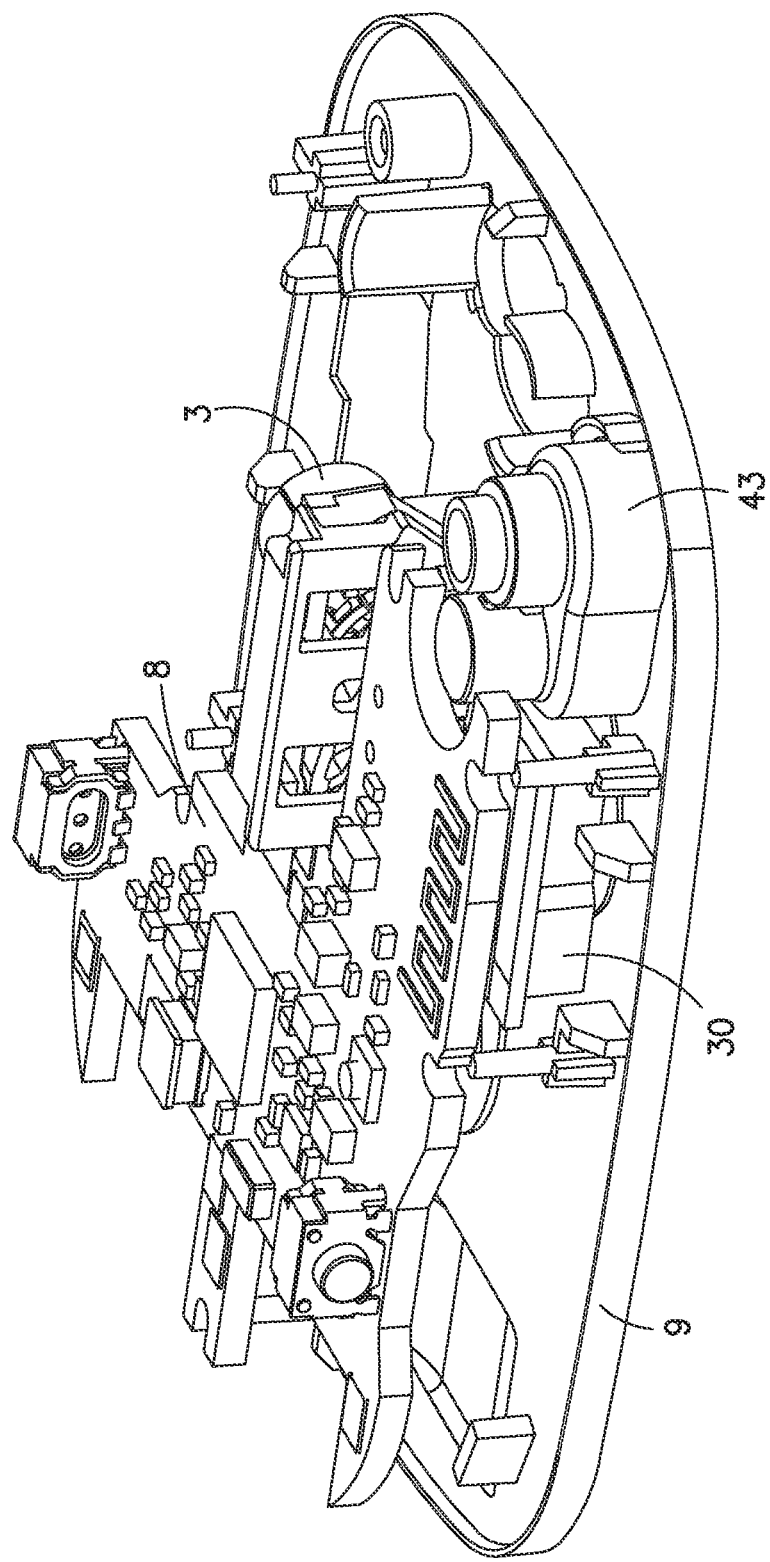
FIG. 30 is a perspective and partially exploded view of a pump employing a pressure sensor such as a microelectromechanical (MEMS) pressure sensor in accordance with another embodiment of the present invention.
Figure 31:
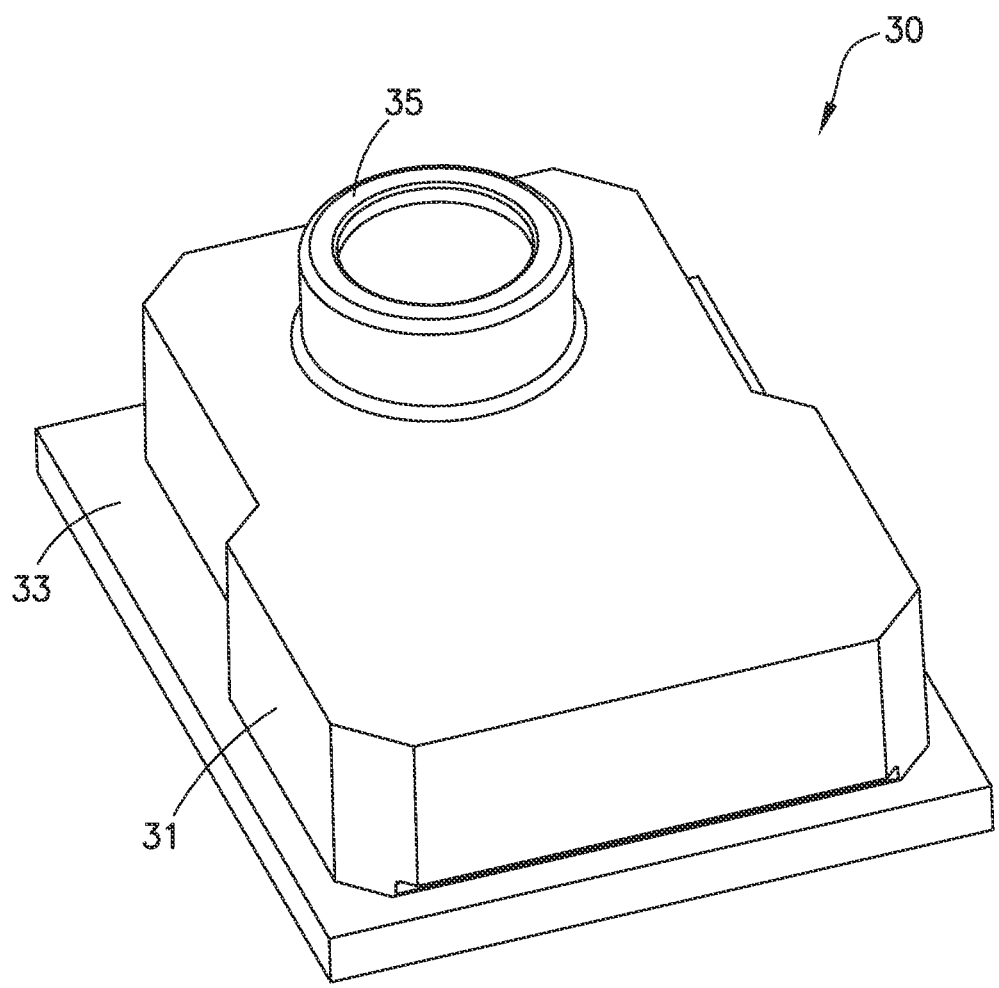
FIG. 31 is a perspective view of a MEMS pressure sensor configured in accordance with an embodiment of the present invention for use with the pump of FIG. 30.

With reference to FIGS. 30 and 31, a MEMS-type pressure sensor 30 can be used in a similar arrangement with respect to the base sensing cavity 29' as described above in connection with a force sensing resistor-type sensor and FIG. 27. MEMS sensors typically come prepackaged by a manufacturer. MEMS sensors contain not only the specific MEMS sensing component, which is necessarily very small, but also related electronics and circuitry. Examples of a MEMS-type pressure sensor 30 are a pressure sensor available from Amphenol Advanced Sensors or MEMS Pressure Sensors Puerto Rico LLC.

As shown in FIG. 31, a MEMS-type pressure sensor 30 can have an enclosure 31 with a cylindrical protrusion 35. A MEMS sensing element is provided within the cylindrical protrusion 35, and associated electronics can be housed in the enclosure 31 which has conductive pads or traces for electrical connection to the PCB 8 (e.g., by a spring or z-axis connector or other means as described above in connection with FIGS. 27, 28 and 29) to provide sensed pressure data to a processor circuit on the PCB 8 and receive power as necessary.

The cylindrical protrusion 35 of the MEMS-type pressure sensor 30 can be mechanically depressed into the base cavity 29' and adhesively or otherwise bonded or mounted to the raised portion 29 or surrounding area of the base 9 such that a seal is created to prevent leakage of fluid from the fluid channel 26 and cavity 29' into the interior 12 of the pump 1. The protrusion 35 is provided with a dielectric gel that protects the MEMS membrane on the chip in the sensor 30 in certain applications (e.g., heart monitoring) that is biocompatible with insulin in the pump.

Any suitable flow sensor, including preferably Micro-Electro-Mechanical Systems (MEMS) flow sensors, could be utilized to provide an informatically-enabled drug delivery device such as a patch pump. Flow sensing, particularly MEMS flow sensors, can include coriolis, capacitance, and thermal sensors such as Time of Flight (ToF) sensors used to determine the volume of drug delivered by a drug delivery device such as a patch pump, as well as sensing conditions such as occlusion or low volume.

Figure 33:
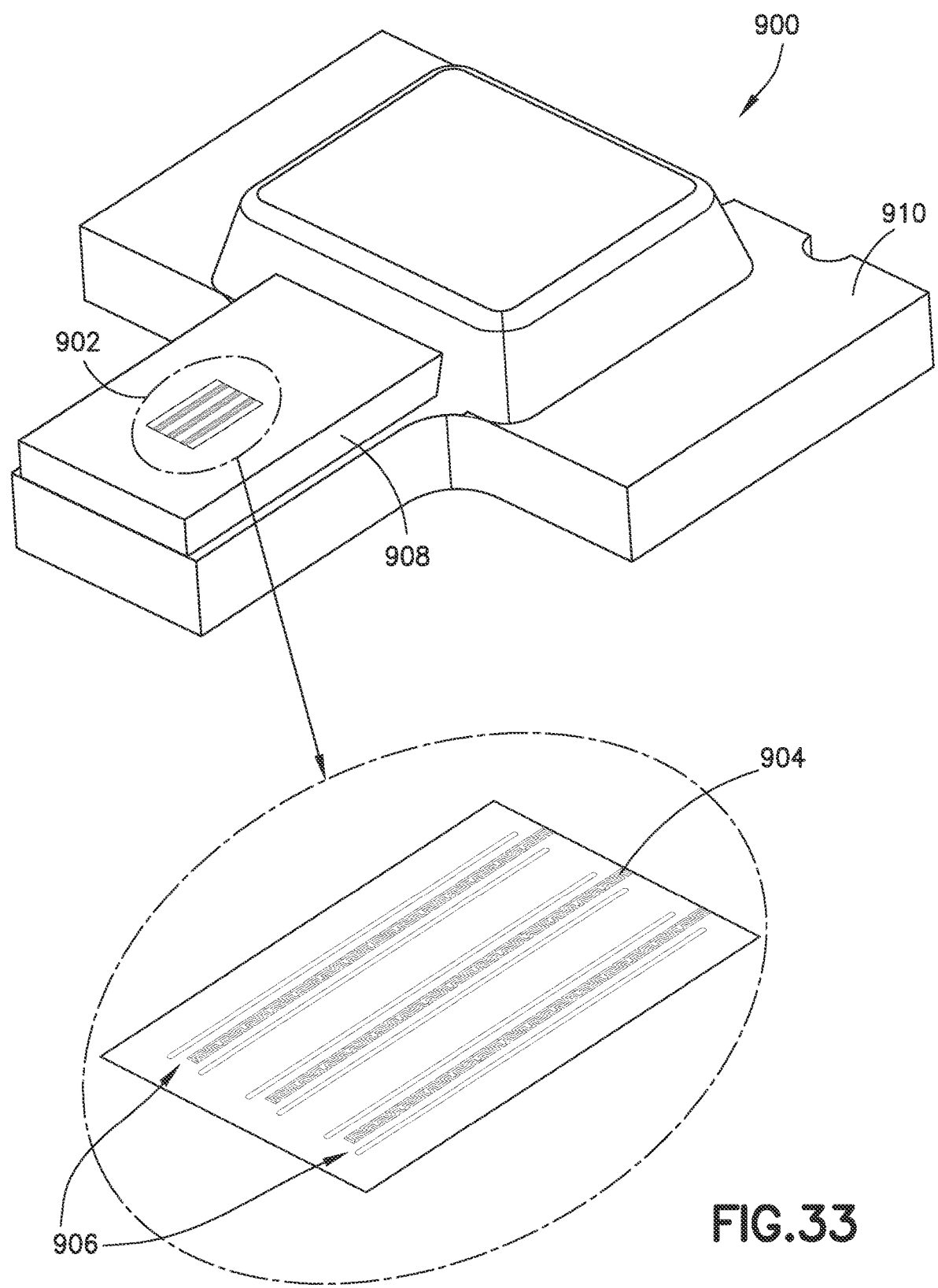
FIG. 33 illustrates a thermal time of flight sensor configured for use in a pump in accordance with an embodiment of the present invention.

An example of a thermal sensor, such as a MEMS thermal time-of-flight flow sensor 900 is illustrated in FIG. 33. Its principals of operation are such that time delay for heat pulses to travel from an input heating element to a downstream sensing element are preferably used to determine a phase shift. The magnitude and phase shift of measurements at the sensing element are preferably used to determine insulin flow. The sensing element consists of a MEMS chip 902 bonded to a circuit board 908. The MEMS chip 902 is a ceramic or glass substrate with conductive traces for a heater 904 and two symmetrically offset temperature sensing elements 906. The center heating element 904 is heated via electric current, and the two outside elements 906 are used to measure the thermal signal created by this heater. The circuit board 908 provides structural support and makes electrical connections to the MEMS sensor chip 902. The two sensing elements 906 are preferably symmetrically offset from heating element 904. Modifying the offset distance permits selection of a particular flow rate range that exhibits large phase resolution, yielding better accuracy. In addition, multiple sensing element pairs may be provided at different offset distances, such as 100 um and 200 um, to extend to larger flow rate ranges as needed.

Figure 28A:
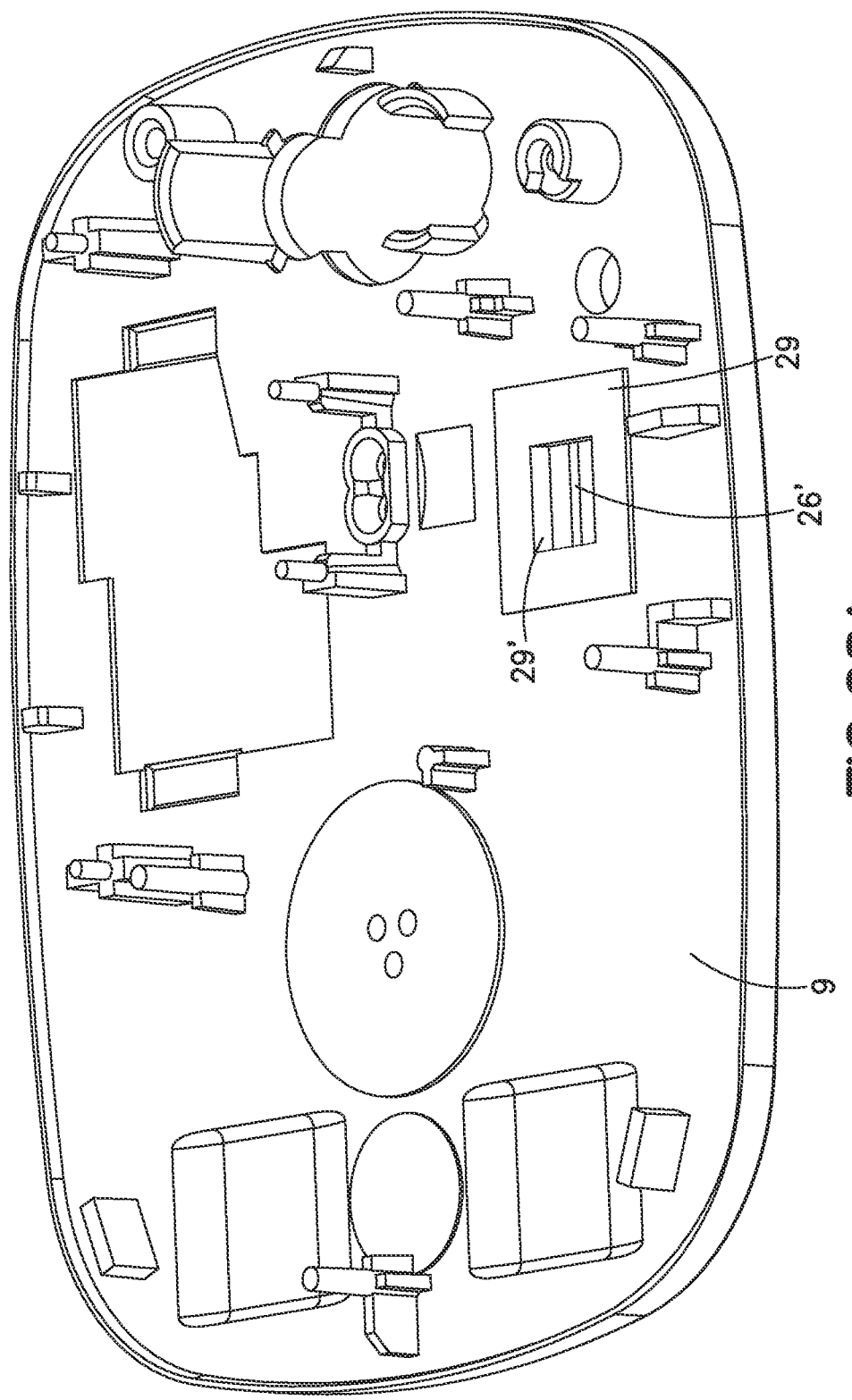
FIG. 28A is a perspective top view of a base of a pump that can be employed a pump in accordance with another embodiment of the present invention.

The MEMS thermal time-of-flight flow sensor 900 has a base 910 which can be provided with conductive pads or traces for electrical connection to the PCB 8 in the patch pump 1. The base 9 can be configured with a rectangular raised portion 29 having a rectangular sensing cavity 29' as shown in FIG. 28A that is dimensioned to allow the MEMS chip 902 bonded to a circuit board 90 to be in contact with the fluid in an exposed fluid path portion such as portion 26'. Alternatively, the MEMS thermal time-of-flight flow sensor 900 can be configured to be seated within the exposed portion 26' and therefore without using a raised portion 29. In either arrangement, the area around the sensing area of the chip is sealed as described above in connection with FIG. 30 to prevent leakage from the fluid path into the interior 12 of the patch pump.

A film that is biocompatible with the fluid (e.g., insulin) can be provided between the sensing area of the MEMS chip 902 and the fluid in the exposed portion 26' to prevent direct contact between the sensor 900 and the fluid. The film can be a z-axis film. The film is, for example, a composite of thermally conductive particles, flakes or fibers embedded in a low thermal conductivity surrounding matrix. The composition of the film allows for relatively high thermal conductivity in the direction perpendicular to the plane of the film and much lower thermal conductivity in the direction along the plane of the film. Thus, the heater 904 can send pulses of heat through the film and into the fluid, where it is carried downstream by fluid flow. The heat is then conducted in the opposite direction through the film to the thermal sensor 906. The film can be elastic or slightly compliant so that it can conform to the surface of the MEMS sensor and eliminate air gaps in order to minimize thermal resistance at the interface without cracking, fracturing or leaking. Pressure from the fluid channel would ensure that the film was firmly pressed against the surface of the MEMS chip during operation and minimize thermal contact resistance. The z-axis film sheet preferably bonds to ABS or other common thermoplastics. A hermetic seal is required between the film and the surface of the base 9 or raised portion 29. The film is stable when exposed to insulin for at least up to five days, and does not release harmful substances into the fluid stream. Biocompatible coatings or surface treatments may be applied to the base of the z-axis film to improve insulin and biocompatibility. Examples of z-axis films presently manufactured, and potentially suitable for use with embodiments of the preset invention include Adhesives Research (EL-9032), 3M (9882), Btech (TP-1), Shin Etsu (Type AF) and Shin Etsu (Type MAF).

In general, the sensor(s) 30 described in connection with FIGS. 27 and 30 can be configured to sense any kind of physical or chemical parameter value that may be relevant to the drug being administered or conditions for delivery or dispensing of the fluid such has, but not limited to, pressure, force, temperature, electrical resistance or conductivity, pH, oxygen or other constituent level, flow, and so on. For example, sensor(s) for various pump parameters may be flow, thermal, time of flight, pressure, or other sensors known in the art, and may be fabricated (at least in part) from parylene—a biocompatible, thin-film polymer. Multiple pressure sensors may be used, for example, to detect a difference in pressure and calculate the flow rate based on a known laminar relationship.

The present invention has been described with reference to certain exemplary embodiments thereof. However, it will be readily apparent to those skilled in the art that it is possible to embody the invention in specific forms other than those of the exemplary embodiments described above. This can be done without departing from the spirit and scope of the invention. The exemplary embodiments are merely illustrative and should not be considered restrictive in any way.

The invention claimed is:

1. A fluid delivery system comprising:
a fluid reservoir;
a pump that controls the flow of fluid from the fluid reservoir to a patient via a fluid path;
a sensor located along the fluid path to detect fluid flow or pressure, the fluid path having a cavity adjacent a portion of the fluid path such that the fluid path is exposed within the cavity; and
a processor configured to control the pump to deliver the fluid to the patient and to receive sensor data from the sensor;
wherein the sensor comprises a protrusion on a sensor enclosure, the protrusion is configured to extend away from the sensor enclosure and into the cavity, and the cavity is dimensioned such that an exterior distal end of the protrusion is within the cavity and volume of the fluid in the cavity is minimized when the exterior distal end of the protrusion is disposed within the cavity, and
wherein, when the protrusion is disposed within the cavity, the protrusion is exposed to the fluid in the fluid path to allow contact between the fluid and the sensor to detect the fluid flow or pressure, the sensor enclosure having electronics for generating sensor data corresponding to the detected fluid flow or pressure, the electronics configured to be connected to the processor to provide the sensor data to the processor.

2. The fluid delivery system of claim 1, wherein the protrusion is provided with a gel to protect the electronics from the fluid.

3. The fluid delivery system of claim 1, wherein the sensor is a pressure sensor.

4. The fluid delivery system of claim 3, wherein the sensor is a force sensing resistor-type sensor, and the fluid in the cavity contacts the exterior of the sensor and pressure is determined from changes in pressure on a surface of the force sensing resistor sensor.

5. The fluid delivery system of claim 1, wherein the sensor is positioned in communication with the fluid at one or more of a pump intake and a pump outlet associated with the pump.

6. The fluid delivery system of claim 5, further comprising an insertion mechanism for inserting a cannula into the skin of the patient to deliver the fluid;
wherein the sensor is positioned downstream of the pump between the pump and the insertion mechanism to determine pressure at the outlet of the pump.

7. The fluid delivery system of claim 6, further comprising:
a planar base that supports the pump and the insertion mechanism;
wherein the fluid path comprises at least one channel embedded on a surface of the planar base and extending between the pump and the insertion mechanism.

8. The fluid delivery system of claim 7, further comprising a fluid channel cover that covers the at least one channel embedded on the surface of the planar base.

9. The fluid delivery system of claim 7, wherein the fluid channel cover is chosen from a clear film, a foil, a flexible sheet of material, a semi-rigid material, and a rigid material.

10. The fluid delivery system of claim 1, wherein an exterior surface of the sensor contacts the fluid in the fluid path.

* * * * *